United States Patent

Yous et al.

[11] Patent Number: 5,386,034
[45] Date of Patent: Jan. 31, 1995

[54] 2-(ALKOXY BENZOTHIAZOLINON-3YL) ETHYLAMINES

[75] Inventors: Said Yous, Lille; Isabelle Lesieur, Gondecourt; Patrick Depreux, Armentieres; Daniel H. Caignard, Paris; Béatrice Guardiola, Neuilly sur Seine; Gérard Adam, Le Mesnil le Roi; Pierre Renard, Versailles, all of France

[73] Assignee: Adir et Compagnie, Courbevoie, France

[21] Appl. No.: 78,001

[22] Filed: Jun. 15, 1993

Related U.S. Application Data

[62] Division of Ser. No. 848,373, Mar. 9, 1992, Pat. No. 5,240,919.

[30] Foreign Application Priority Data

Mar. 25, 1991 [FR] France ............... 91 03538

[51] Int. Cl.⁶ .......................................... C07D 277/68
[52] U.S. Cl. ......................... 548/169; 548/165; 548/173
[58] Field of Search ........... 504/267; 548/165, 169, 548/173

[56] References Cited

U.S. PATENT DOCUMENTS

| | | | |
|---|---|---|---|
| 3,050,526 | 8/1962 | Lo | 548/169 |
| 3,661,921 | 5/1972 | Umio | 546/198 |
| 3,993,468 | 11/1976 | D'Amico | 548/170 |
| 4,227,915 | 10/1980 | D'Amico | 548/171 |
| 4,228,292 | 10/1980 | D'Amico | 548/173 |
| 4,353,919 | 10/1982 | Engel et al. | 548/169 |
| 4,427,436 | 1/1984 | D'Amico | 548/170 |
| 4,460,581 | 7/1984 | Schromm | 548/221 |
| 4,474,965 | 10/1984 | D'Amico | 548/165 |
| 4,554,284 | 11/1985 | Stringer et al. | 514/367 |
| 4,558,060 | 12/1985 | Caignard | 548/221 |
| 4,578,477 | 3/1986 | D'Amico | 548/165 |
| 4,675,331 | 6/1987 | Hume | 514/367 |
| 4,888,428 | 12/1989 | Haga | 548/170 |
| 5,084,469 | 1/1992 | Lesieur et al. | 514/367 |
| 5,132,305 | 6/1992 | Lesieur et al. | 514/365 |
| 5,147,883 | 9/1992 | Aichaioui et al. | 548/221 |
| 5,162,350 | 11/1992 | Lesieur | 514/367 |
| 5,300,507 | 4/1994 | Yous et al. | 514/253 |

FOREIGN PATENT DOCUMENTS 2667068 3/1992 France .

OTHER PUBLICATIONS

D'Amico et al. J. Heterocyclic Chemistry 26(5), 1245-1253 (1989)—cf. compound 12 on p. 1246.

*Primary Examiner*—Donald G. Daus
*Attorney, Agent, or Firm*—Gordon W. Hueschen

[57] ABSTRACT

Compounds of general formula (I):

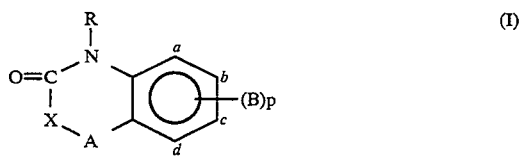

where R, X, A, B and p are defined in the description.

Medicinal products. Useful for treating sleep disorders comprising the same.

3 Claims, No Drawings

2-(ALKOXY BENZOTHIAZOLINON-3YL) ETHYLAMINES

The present application is a division of our prior-filed copending application Ser. No. 07/848,373, filed Mar. 9, 1992, now U.S. Pat. No 5240919, issued Aug. 31, 1993.

The present invention relates to new heterocycle-substituted alkylamides, to a process for preparing them and to pharmaceutical compositions containing them.

Very few heterocycle-substituted alkylamides containing a benzoxazolinone, benzothiazolinone or benzoxazinone unit have been described. Moreover, some benzoxazolinone- or benzothiazolinone-substituted 2-haloacetamides, described as herbicides, are known (U.S. Pat. Nos. 4,311,858, 4,258,196).

The Applicant has now discovered new heterocycle-substituted ethylamides which possess the property of binding with very high affinity to melatonin receptors. This feature makes the compounds of the invention advantageous in disorders of the central nervous system—in particular as anxiolytics and antipsychotics—and of the cerebral circulation and as analgesics. The compounds of the invention are also capable of being used as ovulation regulators, as well as in the treatment of some cancers on account of their immunostimulatory properties.

More especially, the invention relates to the compounds of general formula (I):

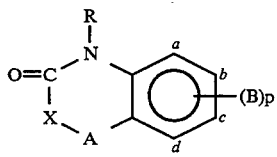

in which:

A represents an oxygen or sulfur atom,
X represents a $CH_2$ group or a single bond,
R represents:
  either a hydrogen atom or a lower alkyl group, and in this case p=1 and B represents an arrangement —$CH_2$—$CH_2$—$NR_1$—CO—$R_2$ where $R_1$ represents a hydrogen atom or a linear or branched lower alkyl group,
and $R_2$ represents:
  a hydrogen atom,
  a cycloalkyl or linear or branched lower alkyl group, optionally substituted with a halogen atom,
  a cycloalkyl group substituted with a linear or branched lower alkyl group,
  an aryl or heteroaryl or aryl(lower alkyl) or substituted aryl or substituted heteroaryl or substituted arylalkyl group, on the understanding that heteroaryl group is understood to mean an unsaturated mono- or bicyclic group comprising from 1 to 3 hetero atoms chosen from nitrogen, oxygen or sulfur, each ring being 4-or 5-membered,
  a group of formula:

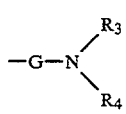

G representing a linear or branched lower alkyl group,
$R_3$ and $R_4$, which may be identical or different, each represent a lower alkyl group or a hydrogen atom or a phenyl or phenyl (lower alkyl) group, or $R_3$ and $R_4$, with the nitrogen atom to which they are attached, form a mono- or bicyclic, aromatic or non-aromatic heterocyclic system optionally comprising another hetero atom chosen from nitrogen, oxygen or sulphur and optionally substituted with one or more lower alkyl or oxo, aryl or aryl (lower alkyl), or substituted aryl or substituted aryl (lower alkyl) groups, on the understanding that, in the definitions of $R_2$, $R_3$ and $R_4$, the term substituted qualifying aryl and arylalkyl and heteroaryl groups means that these groups are substituted with one or more radicals chosen from lower alkyl, lower alkoxy, trifluoromethyl or halogen atom, or alternatively $R_1$, with $R_2$ and the group N—CO, forms a heterocyclic system of formula:

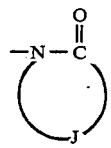

with J being a linear or branched alkyl radical comprising from 2 to 8 carbon atoms, * or an arrangement $(CH_2)_2$—$NR_1$—CO—$R_2$ with $R_1$ and $R_2$ having the same definition as above, and in this case p equals 0 or 1 and B represents a lower alkoxy group, where appropriate their isomers, epimers and diastereoisomers as well as, where appropriate, their addition salts with a pharmaceutically acceptable acid or base, on the understanding that lower alkyl and lower alkoxy mean groups comprising from 1 to 6 carbon atoms and that cycloalkyl means groups comprising from 3 to 8 carbon atoms.

Among pharmaceutically acceptable acids which can, where appropriate, be added to the compounds of formula (I) to obtain a salt, hydrochloric, sulfuric, tartaric, maleic, fumaric, oxalic, methanesulfonic and camphoric acids, and the like, may be mentioned without implied limitation.

Among pharmaceutically acceptable bases which can, where appropriate, be added to the compounds of formula (I) to obtain a salt, sodium, potassium, calcium or aluminum hydroxides, alkali metal or alkaline earth metal carbonates or organic bases such as triethylamine, benzylamine, diethylamine, tert-butylamine, dicyclohexylamine, arginine, and the like, may be mentioned without implied limitation.

The subject of the present invention is also the process for preparing the compounds of formula (I), wherein:

when B is other than an arrangement —$CH_2$—$CH_2NR_1COR_2$, a compound of formula (II):

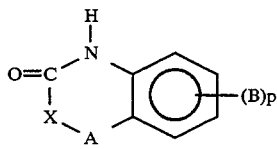

in which A, B, p and X have the same definition as in the formula (I) except for the case where B represents an arrangement —CH$_2$—CH$_2$—NR$_1$COR$_2$, is used as starting material, which compound is treated with an alkali metal agent to obtain a compound of formula (III):

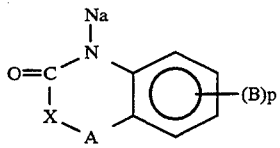

which is treated:
either with a compound of formula (IV/A):

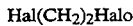
Hal(CH$_2$)$_2$Halo                                    (IV/A)

where Hal and Halo, which may be identical or different, represent a halogen atom, to obtain a compound of formula (V/A):

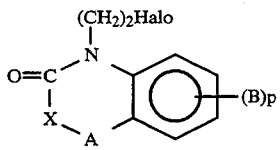

in which A, X, B, p and Halo have the same meaning as above, which is treated with an amine of formula HNR$_1$ where R$_1$ has the same definition as in the formula (I), to obtain a compound of formula (VI):

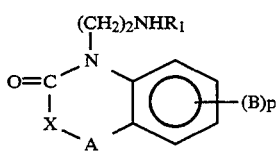

in which A, B, p, R$_1$ and X have the same definition as above,
or with a compound of formula (IV/B):

HalCH$_2$CN                                             (V/B)

in which Hal has the same meaning as above, to obtain a compound of formula (V/B):

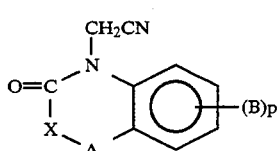

in which X, A, B and p have the same meaning as above,
which compound of formula (V/B) is subjected to a reducing agent and then, when R$_1$ represents a lower alkyl group in the compound of formula (I) which it is desired to obtain, to an alkylating agent, to obtain a compound of formula (VI) as defined above,
which compound of formula (VI) is treated:
either with a compound of formula (VII):

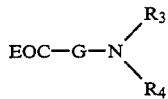

in which E denotes a leaving group chosen from hydroxyl, lower alkoxy or halogen, G, R$_3$ and R$_4$ having the same meaning as in the formula (I), optionally in the presence of an alkaline agent, to yield a compound of formula (I/A), a special case of the compounds of formula (I):

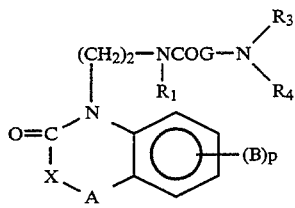

in which A, B, X, R$_1$, R$_3$, R$_4$, G and p have the same definition as above, R$_2$ here denoting a group:

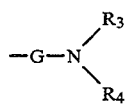

on condition that B does not represent a group:

—CH$_2$—CH$_2$NR$_1$—COR$_2$ which is purified, if so desired, by conventional techniques such as chromatography or crystallization and which is salified, if so desired, with a pharmaceutically acceptable acid,
or with an acid chloride of formula (IX):

Cl—CO—R'$_2$                                            (IX)

or with the corresponding acid anhydride,
R'$_2$ here denoting:
 a cycloalkyl or linear or branched lower alkyl group optionally substituted with a halogen atom, or a cycloalkyl group substituted with a linear or branched lower alkyl group,
 an aryl or heteroaryl or aryl(lower alkyl) group optionally substituted with one or more halogen atoms or groups chosen from lower alkyl, lower alkoxy or trifluoromethyl, the term heteroaryl having the same meaning as above,
yield a compound of formula (I/B):

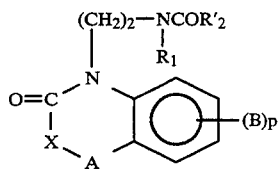

a special case of the compounds of formula (I) in which m, X, A, B, p, R$_1$ and R'$_2$ have the same definition as above, it not being possible for B to represent an arrangement —CH$_2$—CH$_2$—NR$_1$COR$_2$, which is purified, if necessary, by conventional techniques such as chromatography and/or crystallization, which compound of formula (I/B), in the case where R'₂ represents a linear or branched lower alkyl group substituted with a halogen atom, may be subjected, if so desired, to the action of an amine of formula (X):

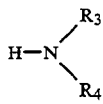   (X)

in which R₃ and R₄ have the same definition as above, in excess or in the presence of a tertiary amine or an alkali metal salt, to yield a compound of formula (I/A) as defined above, which, if so desired, is purified by a conventional technique such as chromatography and/or crystallization, and/or salified with a pharmaceutically acceptable acid, which compound of formula (I/B), when R'₂ represents a linear or branched alkyl substituent comprising at least two carbon atoms and substituted with a halogen atom, and when R₁ simultaneously represents a hydrogen atom, may be subjected, if so desired, to the action of a strong base and preferably an alkali metal alcoholate to yield a compound of formula (I/C):

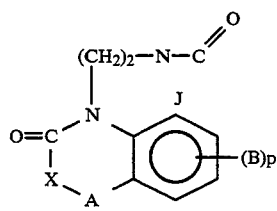   (I/C)

in which B, p, X and A have the same meaning as above, on the understanding that B cannot represent a group —CH₂—CH₂NRCOR₂ and J represents a linear or branched alkyl group comprising from 2 to 8 carbon atoms, a special case of the compounds of formula (I) for which R₁ and R₂ with NCO form a monocyclic system substituted with an oxo group and optionally substituted with one or more lower alkyl groups, which is purified, if so desired, by a technique chosen from crystallization or chromatography, when B represents an arrangement —CH₂—CH₂NR₁COR₂ and p represents 1, a compound of formula (VIII):

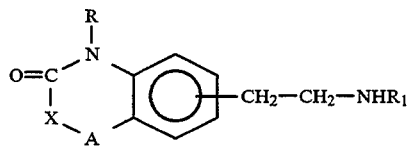   (VIII)

in which R₁, R, X and A have the same definition as in the formula (I), these compounds being described in Patent Application FR 90/11,866 (Corresponding to U.S. Ser. No. 07/765, 959, filed Sep. 26, 1991, now U.S. Pat. No. 5,196,434, issued Mar. 23, 1993), and in U.S. Pat. Nos. 4,554,284 and 4,558,060, is used as starting material, which compound is treated:
either with a compound of formula (VII):

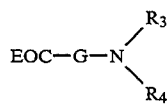   (VII)

in which E denotes a leaving group chosen from hydroxyl, lower alkoxy or halogen, G, R₃ and R₄ having the same meaning as in the formula (I), optionally in the presence of an alkaline agent, to yield a compound of formula (I/D), a special case of the compounds of formula (I):

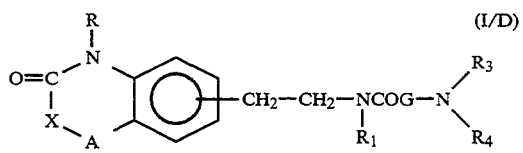   (I/D)

in which X and A, R₁, R₃, R₄ and G have the same definition as above and R represents a hydrogen atom or a lower alkyl group, R₂ here denoting a group:

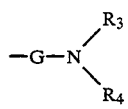

which is purified, if so desired, by conventional techniques such as chromatography and/or crystallization and which is salified, if so desired, with a pharmaceutically acceptable acid or, when R represents a hydrogen atom, with a pharmaceutically acceptable base, or with an acid chloride of formula (IX):

Cl—CO—R'₂   (IX)

or with the corresponding acid anhydride,

R'₂ here denoting:
a cycloalkyl or linear or branched lower alkyl group optionally substituted with a halogen atom, or a cycloalkyl group substituted with a linear or branched lower alkyl group,
an aryl or heteroaryl or aryl(lower alkyl) group optionally substituted with one or more halogen atoms or groups chosen from lower alkyl, lower alkoxy or trifluoromethyl, the term heteroaryl having the same meaning as above, to yield a compound of formula (I/E):

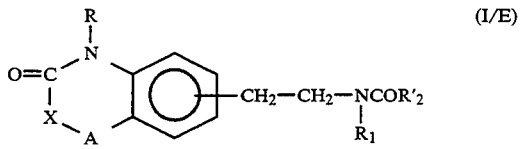   (I/E)

a special case of the compounds of formula (I) in which R₁, X, A and R'₂ have the same definition as above and R represents a lower alkyl group or a hydrogen atom, which is purified, if necessary, by conventional techniques such as chromatography and/or crystallization and which is salified, if so desired, with a pharmaceutically acceptable base when R represents a hydrogen atom, which compound of formula (I/E), in the case where R'$_2$ represents a linear or branched lower alkyl group substituted with a halogen atom, may be subjected, if so desired, to the action of an amine of formula (X):

in which R$_3$ and R$_4$ have the same definition as above, in excess or in the presence of a tertiary amine or an alkali metal salt, to yield a compound of formula (I/D) as defined above, which, if so desired, is purified by a conventional technique such as chromatography and/or crystallization, and/or salified with a pharmaceutically acceptable acid, which compound of formula (I/E), when R'$_2$ represents a linear or branched alkyl substituent comprising at lest two carbon atoms and substituted with a halogen atom, and when R$_1$ simultaneously represents a hydrogen atom, may be subjected, if so desired, to the action of a strong base and preferably an alkali metal alcoholate to yield a compound of formula (I/F):

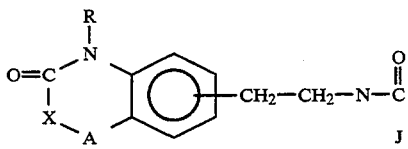

in which R represents a hydrogen atom or a lower alkyl group, X and A have the same meaning as above and J represents a linear or branched alkyl group comprising from 2 to 8 carbon atoms, a special case of the compounds of formula (I) for which R$_1$ and R$_2$ with NCO form a monocyclic system substituted with an oxo group and optionally substituted with one or more lower alkyl groups, which is purified, if so desired, by a technique chosen from crystallization or chromatography and which is salified, if so desired, when R represents a hydrogen atom, with a pharmaceutically acceptable base.

The products of formula (VI) are new and form part of the invention on the same basis as the products of formula (I), for which they constitute synthesis intermediates, except for the compounds for which:

X represents a single bond,

A represents a sulfur atom and p represents 0.

The products of formulae (V/A) and (V/B) for which p is other than 0 are also new, and also form part of the invention on the same basis as the products of formula (I), for which they constitute synthesis intermediates.

Another special case relates to the compounds of formula (I/K):

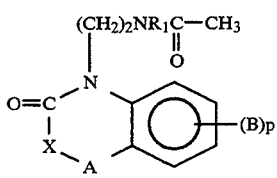

which is obtained in a single step by catalytic reduction of the compounds of formula (V/K) in an acetic anhydride medium:

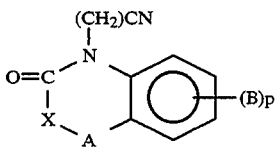

followed, if necessary, by purification and, when R$_1$ represents a lower alkyl group, by treatment with an alkylating agent.

The compounds of formula (I) possess advantageous pharmacological properties.

A pharmacological study of the compounds of the invention showed, in effect, that they are of low toxicity and endowed with appreciable affinity for melatonin receptors, and that, in addition, they substantially increase melatonin synthesis by the pineal gland. Furthermore, they possess considerable activity in relation to the central nervous system and, in particular, sedative, anxiolytic, antipsychotic and analgesic properties as well as effects on the microcirculation have been noted, these enabling it to be established that the products of the invention are useful in the treatment of stress, sleep disorders, anxiety, seasonal depression, insomnia and fatigue due to jet lag, schizophrenia, panic attacks, melancholia, appetite regulation, insomnia, psychotic disorders, epilepsy, Parkinson's disease, senile dementia, the various disorders linked to normal or pathological aging, migraine, memory loss, Alzheimer's disease and also disorders of the cerebral circulation.

In another sphere of activity, it is apparent that the products of the invention possess ovulation-inhibiting properties, and immunomodulatory properties and that they are hence capable of being used in the treatment of certain cancers, and that, when administered externally, they are useful in the treatment of psoriasis, acne and seborrhea, protect the skin and promote hair growth. They can also have a veterinary application owing to their effect on the coat.

The subject of the present invention is also pharmaceutical compositions containing the products of formula (I) or, where appropriate, one of their addition salts with a pharmaceutically acceptable acid, alone or in combination with one or more pharmaceutically acceptable, non-toxic, inert excipients or vehicles.

Among the pharmaceutical compositions according to the invention, there may be mentioned, more especially, those which are suitable for oral, parenteral, nasal, per- or transcutaneous, rectal, perlingual, ocular or respiratory administration, and in particular simple or sugar-coated tablets, sublingual tablets, sachets, packets, hard gelatin capsules, sublingual preparations, troches, suppositories, creams, ointments, skin gels, ampuls for oral use or injection, and the like.

The dosage varies according to the patient's age and weight, the administration route and the nature of the therapeutic indication or of any associated treatments, and ranges between 0.1 mg and 1 gram per 24 hours.

The examples which follow illustrate the invention but in no way limit it.

EXAMPLE 1

N-[2-(6-Methoxy-3-Benzoxazolinonyl)Ethyl]Acetamide

STAGE A (6-METHOXY-3-BENZOXAZOLINONYL)ACETONITRILE 0.1 gram-atom of sodium is added in small pieces with magnetic stirring into a 250-cm$^3$ round-bottomed flask containing 100 cm3 of absolute ethanol.

The mixture is left stirring until the sodium has dissolved completely. 0.1 mol of 6-methoxybenzoxazolinone is added, stirring is continued for 30 minutes and the mixture is then taken to dryness.

The sodium derivative obtained is solubilized in 80 cm$^3$ of anhydrous dimethylformamide. With magnetic stirring, 0.12 mol of chloroacetonitrile is added via a dropping funnel. The reaction mixture is heated to 80° C. for 1 hour 30 minutes. It is allowed to cool and then poured into 400 cm$^3$ of ice-cold water.

The precipitate formed is drained, washed until the washing liquors are neutral, dried and recrystallized.

Recrystallization solvent: 95° strength alcohol Yield: 95% Melting point: 142°-143° C. Elemental analysis:

|  | C % | H % | N % |
|---|---|---|---|
| Calculated: | 58.82 | 3.95 | 13.72 |
| Found: | 58.73 | 3.82 | 13.69 |

Infrared spectrometry: (3060-2940) cm$^{-1}$, $\nu$ C—H 1770 cm$^{-1}$, $\nu$ CO(O—CO—N) 1630 cm$^{-1}$, $\nu$ C$=$C (aromatic) Nuclear Magnetic Resonance Spectrometry (CDCl$_3$): 3.85 ppm, (s, 3H), OCH$_3$ 4.75 ppm, (s, 2H), CH$_2$—CN 6.80 ppm, (unresolved peaks, 2H), H$_4$, H7.05 ppm, (d, 1H), H$_7$

STAGE B  2-(6-METHOXY-3-BENZOXAZOLINONYL)ETHYLAMINE HYDROCHLORIDE

In a round-bottomed flask, 0.03 mol of (6-methoxy-3-benzoxazolinonyl)acetonitrile is dissolved with magnetic stirring in 50 cm3 of tetrahydrofuran at room temperature.

0.05 mol of methylborane sulfide is added slowly under a nitrogen atmosphere using a dropping funnel. The mixture is heated to reflux for 30 minutes. It is cooled in an ice bath, and 30 cm$^3$ of 6N hydrochloric acid solution are then added very slowly. The mixture is heated to reflux for 30 minutes.

It is allowed to cool, and the precipitate formed is drained, washed with 30 cm$^3$ of acetone, dried and recrystallized in a suitable solvent.

Recrystallization solvent: 95° strength alcohol Yield: 83% Melting point: >260° C. Infrared spectrometry: (3120-2500 ) cm$^{-1}$, $\nu$ NH$_2$ salt 1770 cm$^{-1}$, $\nu$ CO(O—CO—N) (1635-1620 ) cm$^{-1}$, $\nu$ C$=$C (aromatic) Nuclear Magnetic Resonance Spectrometry(CDCl$_3$): 3.25 ppm, (t, 2H), $\underline{CH_2}$—NH$_2$ 3.75 ppm, (s, 3H), OCH$_3$ 4.15 ppm, (t, 2H), $\overline{=N}$—CH$_2$ 6.82 ppm, (dd, 1H), H$_5$ 7.00 ppm, (d, 1H), H$_7$ 7.40 ppm, (d, 1H), H$_4$ 8.40 ppm, (signal, 2H), NH$_2$ disappears in D$_2$O

STAGE C

N-[2-(6-METHOXY-3-BENZOXAZOLINONYL)ETHYL]ACETAMIDE 0.02 mol of 3-(2-aminoethyl)-6-methoxybenzoxazolinone hydrochloride is dissolved in a water/chloroform mixture. 0.02 mol of potassium carbonate is added and the mixture is left stirring for 1 hour.

It is cooled in an ice bath, and 0.022 mol of acetyl chloride is then added slowly. The mixture is kept stirring for ½ hour. The chloroform phase is taken to dryness, and the residue is then recrystallized in a suitable solvent.

Recrystallization solvent: Absolute alcohol Yield: 86% Melting point: 162°-164° C. Elemental analysis:

|  | C % | H % | N % |
|---|---|---|---|
| Calculated: | 57.59 | 5.64 | 11.20 |
| Found: | 57.30 | 5.54 | 10.96 |

Infrared spectrometry: 1320 cm$^{-1}$, $\nu$ N—H (3060-2840) cm$^{-1}$, $\nu$ C—H 1765 cm$^{-1}$, $\nu$ CO(O—CO—N) 1640 cm$^{-1}$, $\nu$ CO (amide) 1620 cm$^{-1}$, $\nu$ C$=$C (aromatic) Nuclear Magnetic Resonance Spectrometry (CDCl$_3$): 1.94 ppm, (s, 3H), COCH$_3$ 3.60 ppm, (multiplet, 2H), CH$_2$—CH$_2$NH 3.80 ppm, (s, 3H), OCH$_3$ 3.95 ppm, (t, 2H), N—$\overline{CH_2}$ 6.20 ppm, (signal, 1H), NH 6.65 ppm, (unresolved peaks, 2H), H$_5$, H$_7$ 6.96 ppm, (d, 1H), H$_4$

EXAMPLE 2

N-[2-(5-Methoxy-3-Benzoxazolinonyl)Ethyl]Acetamide

Using the procedure described in Example 1, but replacing 6-methoxybenzoxazolinone in stage A by 5-methoxybenzoxazolinone, the following are obtained:
STAGE A (5-METHOXY-3-BENZOXAZOLINONYL)ACETONITRILE Melting point: 148°-149° C. Yield: 93% Elemental analysis:

|  | C % | H % | N % |
|---|---|---|---|
| Calculated: | 58.82 | 3.95 | 13.72 |
| Found: | 58.55 | 3.71 | 13.61 |

Infrared spectrometry: (3060-2900) cm$^{-1}$, $\nu$ C—H 1790 cm$^{-1}$, $\nu$ CO(O—CO—N) 1620 cm$^{-1}$, $\nu$ C$=$C (aromatic) Nuclear Magnetic Resonance Spectrometry (CDCl$_3$): 3.86 ppm, (s, 3H), OCH$_3$ 4.75 ppm, (s, 2H), CH$_2$—CN 6.70 ppm, (unresolved peaks, 2H), H$_4$, H$_6$ 7.20 ppm, (d, 1H), H$_7$
STAGE B
2-(5-METHOXY-3-BENZOXAZOLINONYL)ETHYLAMINE HYDROCHLORIDE Recrystallization solvent: 95° strength alcohol Yield: 81% Melting point: >260° C. Infrared spectrometry: (3120-2500), $\nu$ NH$_2$ salt 1765 cm$^{-1}$, $\nu$ CO(O—CO—N) 1620 cm$^{-1}$, $\nu$ C$=$C (aromatic) Nuclear Magnetic Resonance Spectrometry (CDCl$_3$): 3.25 ppm, (t, 2H), $=$CH$_2$—CH$_2$—NH$_2$ 3.75 ppm, (s, 3H), OCH$_3$ 4.16 ppm, (t, 2H), $\overline{-CH_2}$—CH$_2$ 6.70 ppm, (dd, 1H), H$_6$ (7-7.40) ppm, (unresolved peaks, 2H), H$_4$, H$_7$ 9.50 ppm (signal, 2H) NH$_2$ disappears in D$_2$O
STAGE C

N-[2-(5-METHOXY-3-BENZOXAZOLINONYL)ETHYL]ACETAMIDE

Recrystallization solvent: Toluene Yield: 87% Melting point: 118°-120° C. Elemental analysis:

|  | C % | H % | N % |
|---|---|---|---|
| Calculated: | 57.59 | 5.64 | 11.20 |

|          | C %   | H %  | N %   |
|----------|-------|------|-------|
| Found:   | 57.50 | 5.57 | 11.26 |

Infrared spectrometry: 3300 cm⁻¹, ν N—H (amide) (3060–2840) cm⁻¹, ν C—H 1765 cm⁻¹, ν CO(O—CO—N) 1655 cm⁻¹, ν CO (amide) 1630 cm⁻¹, ν C≡C (aromatic) Nuclear Magnetic Resonance Spectrometry (CDCl₃): 1.93 ppm, (s, 3H), COCH₃ 3.58 ppm, (multiplet, 2H), CH₂—NH 3.80 ppm, (s, 3H), OCH₃ 3.94 ppm, (t, 2H), CH₂N= 6.25 ppm, (signal, 1H), NH 6.64 ppm, (unresolved peaks, 2H), H₄, H₆ 7.10 ppm, (d, 1H), H₇

EXAMPLE 3

N-[2-(5-Methoxy-3-Benzoxazolinonyl)Ethyl]Isobutyramide

Using the procedure described in Example 2, stage C, but replacing acetyl chloride by isobutyryl chloride, the product of the title is obtained.

Recrystallization solvent: Toluene/Hexane Yield: 82% Melting point: 130°–131° C. Elemental analysis:

|             | C %   | H %  | N %   |
|-------------|-------|------|-------|
| Calculated: | 60.41 | 6.52 | 10.06 |
| Found:      | 60.55 | 6.66 | 10.01 |

Infrared spectrometry: 3300 cm⁻¹, ν N—H (3080–2840) cm⁻¹, ν C—H 1760 cm⁻¹, ν CO(O—CO—N) 1640 cm⁻¹, νCO (amide) 1625 cm⁻¹, ν C≡C (aromatic) Nuclear Magnetic Resonance Spectrometry (CDCl₃): 1.10 ppm, (d, 6H), CH(CH₃)₂ 2.25 ppm, (multiplet, 1H), CH 3.75 ppm, (s, 3H), OCH₃ 6.20 ppm, (signal, 1H), NH 6.60 ppm, (unresolved peaks, 2H), H₄, H₆ 7.10 ppm, (d, 1H), H₇

EXAMPLE 4

N-[2-(6-Methoxy-3-Benzoxazolinonyl)Ethyl]Isobutyramide

Using the procedure described in Example 2, stage C, but replacing acetyl chloride by isobutyryl chloride, the product of the title is obtained.

Recrystallization solvent: Toluene Melting point: 161°–162° C. Yield: 86% Elemental analysis:

|             | C %   | H %  | N %   |
|-------------|-------|------|-------|
| Calculated: | 60.41 | 6.52 | 10.06 |
| Found:      | 60.36 | 6.48 | 10.11 |

Infrared spectrometry: 3300 cm⁻¹, ν N—H (3080–2840) cm⁻¹, ν C—H 1760 cm⁻¹, ν CO(O—CO—N) 1640 cm⁻¹, ν CO (amide) 1625 cm⁻¹, ν C≡C (aromatic)
Nuclear Magnetic Resonance Spectrometry (CDCl₃): 1.10 ppm, (d, 6H), CH(CH₃)₂ 2.25 ppm, (multiplet, 1H), CH 3.60 ppm, (multiplet, 2H), CH₂—NH 3.75 ppm, (s, 3H), OCH₃ 3.95 ppm, (t, 2H), CH₂—N= 6.15 ppm, (signal, 1H), NH 6.65 ppm, (unresolved peaks, 2H), H₅, H₇ 6.95 ppm, (d, 1H), H₄

EXAMPLE 5:

N-[2-(6-Methoxy-3-Benzoxazolinonyl)Ethyl]Phenylacetamide

Using the procedure described in Example 2, but replacing acetyl chloride by phenacetyl chloride, the product of the title is obtained.

Infrared spectrometry: 3300 cm⁻¹, ν N—H 1760 cm⁻¹, ν CO(O—CO—N) Nuclear Magnetic Resonance Spectrometry (CDCl₃): 3.75 ppm, singlet, 3H, OCH₃

EXAMPLE 6:

N-[2-(6-Methoxy-3-Benzoxazolinonyl)Ethyl]-(2-OXO1-Pyrrolidinyl)Acetamide

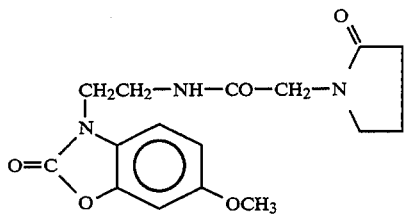

A mixture of 0.02 mol of 3-(2-aminoethyl)-6-methoxybenzoxazolinone and 0.022 mol of methyl (2-oxo-1-pyrrolidinyl)acetate is heated with magnetic stirring to a temperature of 80° C. for 3 hours. The medium is taken up with slightly acid water and the precipitate is drained.

Infrared spectrometry: 33000 cm⁻¹, ν N—H 1760 cm⁻¹, ν CO(O—CO—N) Nuclear Magnetic Resonance Spectrometry (CDCl₃): 3.75 ppm, singlet, 3H, OCH₃

EXAMPLE 7

N-[2-(6-Methoxy3-Benzoxazolinonyl)Ethyl]-4-Chlorobutyramide

Using the procedure described in Example 2, but replacing acetyl chloride by 4-chlorobutyryl chloride, the product of the title is obtained.

Infrared spectrometry: 1760 cm⁻¹, ν CO(O—CO—N) Nuclear Magnetic Resonance Spectrometry (CDCl₃): 3.80 ppm, singlet, 3H, OCH₃

EXAMPLE 8

N-[2-(6-Methoxy-3-Benzoxazolinonyl)Ethyl]-2-Pyrrolidinone 0.01 gram-atom of sodium is dissolved in 50 cm³ of ethanol. N-[2-(6-Methoxy-3-benzoxazolinonyl)ethyl]-4-chlorobutyramide, obtained in the preceding example, is added with magnetic stirring. The mixture is kept stirring for 20 minutes. It is taken to dryness. The residue is solubilized in 40 cm³ of anhydrous dimethylformamide. The mixture is heated to boiling for 7 hours. It is evaporated under vacuum and the residue is taken up with ether. The mixture is filtered and taken to dryness. The product is recrystallized.

Infrared spectrometry: 1760 cm⁻¹, ν CO(O—CO—N) Nuclear Magnetic Resonance Spectrometry (CDCl₃): 3.80 ppm, singlet, 3H, OCH₃

EXAMPLE 9

N-[2-(6-Methoxy-3-Benzoxazolinonyl)Ethyl]-2-Bromoacetamide

The same procedure as in Example 7, replacing 4-chlorobutyryl chloride by bromoacetyl chloride.

EXAMPLE 10

N-[2-(6-Methoxy-3-Benzoxazolinonyl)Ethyl]-2-Morpholinoacetamide 0.01 mol of morpholine is dissolved with magnetic stirring in 50 cm$^3$ of acetone. 0.012 mol of triethylamine and 0.01 mol of N-[2-(6-methoxy-3-benzoxazolinonyl)ethyl]-2-bromoacetamide are added. The mixture is brought to reflux for one hour with magnetic stirring. The precipitate formed is drained and the filtrate is evaporated. The residue is taken up with alkaline water. The precipitate is drained, washed, dried and recrystallized.

Infrared spectrometry: 1760 cm$^{-1}$, $\nu$ CO(O—CO—N)

EXAMPLE 11

N-[2-(6-Methoxy-3-Benzoxazolinonyl)Ethyl]-2-{4-[(2,3,4-Trimethoxyphenyl)Methyl]-1-Piperazinyl-}Acetamide Using the procedure described in the preceding example, but replacing morpholine by 1-[(2,3,4-trimethoxyphenyl)methyl]piperazine, the product of the title is obtained.

EXAMPLE 12

N-[2-(6-Methoxy-3-Benzoxazolinonyl)Ethyl]-N-Methylacetamide

By replacing 2-(6-methoxy-3-benzoxazolinonyl)ethylamine in Example 1 by N-[2-(6-methoxy-3-benzoxazolinonyl)ethyl]-N-methylamine, the product of the title is obtained.

EXAMPLE 13

N-[2-(6-Methoxy-3-Benzoxazolinonyl)Ethyl]Benzamide

By replacing acetyl chloride in Example 1, stage C, by benzoyl chloride, the product of the title is obtained.

Infrared spectrometry: 1760 cm$^{-1}$, $\nu$ CO

EXAMPLE 14

N-[2-(6-Methoxy-3-Benzoxazolinonyl)Ethyl]-Para-Toluenecarboxamide

By replacing acetyl chloride in Example 1, stage C, by para-toluoyl chloride, the product of the title is obtained.

Infrared spectrometry: 1760 cm$^{-1}$, $\nu$ CO

EXAMPLE 15

N-[2-(6-Methoxy-3-Benzoxazolinonyl)Ethyl]-4-Fluorobenzamide

By replacing acetyl chloride in Example 1, stage C, by para-fluorobenzoyl chloride, the product of the title is obtained.

Infrared spectrometry: 1765 cm$^{-1}$, $\nu$ CO

EXAMPLE 16

N-[2-(6-Methoxy-3-Benzoxazolinonyl)Ethyl]-3-(Trifluoromethyl)Benzamide

By replacing acetyl chloride in Example 1, stage C, by 3-(trifluoromethyl)benzoyl chloride, the product of the title is obtained.

Infrared spectrometry: 1760 cm$^{-1}$, $\nu$ CO

EXAMPLE 17

N-[2-(6-Methoxy3-Benzoxazolinonyl)Ethyl]-3,5-Dichlorobenzamide

By replacing acetyl chloride in Example 1, stage C, by 3,5-dichlorobenzoyl chloride, the product of the title is obtained.

EXAMPLE 18

N-[2-(6-Methoxy-3-Benzoxazolinonyl)Ethyl]Isonicotinamide

By replacing acetyl chloride in Example 1, stage C, by isonicotinoyl chloride, the product of the title is obtained.

EXAMPLE 19

N-[2-(6-Methoxy-3-Benzoxazolinonyl)Ethyl]-2-Indolecarboxamide

By replacing acetyl chloride in Example 1, stage C, by 2-indolecarbonyl chloride, the product of the title is obtained.

Infrared spectrometry: 3400 cm$^{-1}$, $\nu$ NH (indole) 1760 cm$^{-1}$, $\nu$ CO

EXAMPLE 20

N-[2-(6-Methoxy-3-Benzoxazolinonyl)Ethyl]-2-(Benzylamino)Acetamide

Using the procedure described in Example 10, and replacing morpholine by benzylamine, the product of the title is obtained.

Infrared spectrometry: 1760 cm$^{-1}$, $\nu$ CO

EXAMPLE 21

N-[2-(6-Methoxy-3-Benzoxazolinonyl)Ethyl]-2-(N', N'-Diethylamino)Acetamide

Using the procedure described in Example 10, but replacing morpholine by N,N-diethylamine, the product of the title is obtained.

Infrared spectrometry: 1765 cm$^{-1}$, $\nu$ CO (OCON)

EXAMPLE 22

N-[2-(6-Methoxy-3-Benzoxazolinonyl)Ethyl]-2-Aminoacetamide Hydrochloride 0.012 mol of hexamethylenetetramine is dissolved with magnetic stirring in 15 cm$^3$ of chloroform, and 0.01 mol of N-[2-(6-methoxy-3-benzoxazolinonyl)ethyl]-2-bromoacetamide, obtained in Example 9, dissolved in 20 cm$^3$ of chloroform, is introduced. The mixture is brought to reflux for 100 hours. The product is drained and dried. The precipitate is introduced into a one necked ground glass flask. 150 cm$^3$ of alcohol and 30 cm$^3$ of concentrated hydrochloric acid are added.

The mixture is brought to reflux for 2 hours. The solvent is evaporated off. The product is recrystallized in 90° strength alcohol.

Infrared spectrometry: 1760 cm$^{-1}$, $\nu$ CO (OCON)

EXAMPLE 23

N-[2-(6-Methoxy-3-Benzoxazolinonyl)Ethyl]-2-[4-(4-Fluorophenyl)-1-Piperazinyl]Acetamide Using the procedure described in Example 10, but replacing morpholine by 1-(4-fluorophenyl)piperazine, the product of the title is obtained.

EXAMPLE 24

N-[2-(6-Methoxy-3-Benzoxazolinonyl)Ethyl]-2-{4-[3-(Trifluoromethyl)Phenyl]-1-Piperazinyl}Acetamide Using the procedure described in Example 10, but replacing morpholine by 1-[3-(trifluoromethyl)phenyl]-piperazine, the product of the title is obtained.

EXAMPLE 25

N-[2-(6-Methoxy-3-Benzoxazolinonyl)Ethyl]Cyclohexanecarboxamide ($R_2$=cyclohexyl)

Using the procedure described in Example 1, but replacing acetyl chloride by cyclohexanecarbonyl chloride, the product of the title is obtained.

EXAMPLE 26

N-[2-(6-Methoxy-3-Benzoxazolinonyl)Ethyl]Formamide 0.01 mol of 2-(6-methoxy-3-benzoxazolinonyl)ethylamine and 0.02 mol of formic acid are placed in a porcelain crucible. The mixture is heated to 120° C. until a dry residue is obtained. The product is recrystallized.

EXAMPLE 27

N-[2-(6-Methoxy-3-Benzoxazolinonyl)Ethyl]Cyclopropanecarboxamide

Using the procedure described in Example 1, but replacing acetyl chloride by cyclopropanecarbonyl chloride, the product of the title is obtained.

EXAMPLE 28

N-[2-(6-Methoxy-3-Benzoxazolinonyl)Ethyl]Pentanamide

Using the procedure described in Example 1, but replacing acetyl chloride by valeroyl chloride, the product of the title is obtained.

EXAMPLE 29

N-[2-(6-Methoxy-3-Benzoxazolinonyl)Ethyl]Cyclobutanecarboxamide

Using the procedure described in Example 1, but replacing acetyl chloride by cyclobutanecarbonyl chloride, the product of the title is obtained.

Using the procedure described in the preceding examples, the following are likewise obtained:

N-[2-(6-METHOXY-3-BENZOXAZOLINONYL)ETHYL]-4-BROMOBUTYRAMIDE
N-[2-(6-METHOXY-3-BENZOXAZOLINONYL)ETHYL]-5-BROMOPENTANAMIDE
N-[2-(6-METHOXY-3-BENZOXAZOLINONYL)ETHYL]-3-BROMOPROPIONAMIDE
N-[2-(6-METHOXY-3-BENZOXAZOLINONYL)ETHYL]-3-MORPHOLINOPROPIONAMIDE
N-[2-(6-METHOXY-3-BENZOXAZOLINONYL)ETHYL]-4-MORPHOLINOBUTYRAMIDE
N-[2-(6-METHOXY-3-BENZOXAZOLINONYL)ETHYL]-4-{4-[(2,3,4-TRIMETHOXYPHENYL)METHYL]-1-PIPERAZINYL}-BUTYRAMIDE
N-[2-(6-METHOXY-3-BENZOXAZOLINONYL)ETHYL]-3-{4-[(2,3,4-TRIMETHOXYPHENYL)METHYL]-1-PIPERAZINYL}-PROPIONAMIDE
N-[2-(6-METHOXY-3-BENZOXAZOLINONYL)ETHYL]-2-PIPERIDONE
N-[2-(6-METHOXY-3-BENZOXAZOLINONYL)ETHYL]-2-BROMOPROPIONAMIDE
N-[2-(6-METHOXY-3-BENZOXAZOLINONYL)ETHYL]-2-{4-[(2,3,4-TRIMETHOXYPHENYL)METHYL]-1PIPERAZINYL}-PROPIONAMIDE

By replacing 2-(6-methoxy-3-benzoxazolinonyl)ethylamine in Examples 5 to 9 by 2-(5-methoxy-3-benzoxazolinonyl)ethylamine, the products of the preceding examples methoxylated, respectively, at position 5 of the benzoxazolinone are obtained instead of the compounds methoxylated at position 6.

EXAMPLE 30

N-[2-(6-methoxy-3-benzothiazolinonyl)ethyl]ACETAMIDE

STAGE A (6-METHOXY-3-BENZOTHIAZOLINONYL)ACETONITRILE

The procedure used is that described in Example 1, stage A, replacing 6-methoxybenzoxazolinone by 6-methoxybenzothiazolinone.

Recrystallization solvent: 95° strength alcohol Yield: 93% Melting point: 168°–169° C. Elemental analysis:

|  | C % | H % | N % |
|---|---|---|---|
| Calculated: | 54.52 | 3.66 | 12.72 |
| Found: | 54.59 | 3.52 | 12.73 |

Infrared spectrometry: (3080–2940) cm$^{-1}$, $\nu$ C—H 1680 cm$^{-1}$, $\nu$ CO(S—CO—N) (1630–1580) cm$^{-1}$, $\nu$ C=C (aromatic) Nuclear Magnetic Resonance Spectrometry (CDCl$_3$): 3.85 ppm, (s, 3H), OCH$_3$ 4.75 ppm, (s, 2H), CH$_2$—CN 6.75 ppm, (unresolved peaks, 2H), H$_4$, H$_5$ 7.30 ppm, (d, 1H), H$_7$

STAGE B 2-(6-METHOXY-3-BENZOTHIAZOLINONYL)ETHYLAMINE HYDROCHLORIDE

The procedure used is that described in Example 1, stage B, replacing (6-methoxy-3-benzoxazolinonyl)acetonitrile by (6-methoxy-3-benzothiazolinonyl)acetonitrile obtained in stage A.

Recrystallization solvent: 95° strength alcohol/water (5:1) Yield: 83% Melting point: >260° C. Infrared spectrometry (3120–2500) cm$^{-1}$, $\nu$ NH$_2$ salt 1640 cm$^{-1}$, $\nu$ CO(S—CO—N) 1600 cm$^{-1}$, $\nu$ C=C (aromatic)

STAGE C

N-[2-(6-METHOXY-3-BENZOTHIAZOLINONYL)ETHYL]ACETAMIDE

The procedure used is that described in Example 1, stage C, replacing 2-(6-methoxy-3-benzoxazolinonyl)ethylamine hydrochloride by 2-(6-methoxy-3-benzothiazolinonyl)ethylamine hydrochloride obtained in stage B.

Recrystallization solvent: Toluene Yield: 80% Melting point.: 152°–154° C. Elemental analysis:

|  | C % | H % | N % |
|---|---|---|---|
| Calculated: | 54.11 | 5.29 | 10.52 |
| Found: | 54.19 | 5.32 | 10.43 |

Infrared spectrometry: 3240 cm$^{-1}$, $\nu$ N—H (3060–2840) cm$^{-1}$, $\nu$ C—H 1675 cm$^{-1}$, $\nu$ CO(-S—CO—N) 1650 cm$^{-1}$, $\nu$ CO (amide) 1580 cm$^{-1}$, $\nu$ C=C (aromatic) Nuclear Magnetic Resonance Spectrometry (CDCl$_3$): 1.94 ppm, (s, 3H), COCH$_3$ 3.80 ppm, (s, 3H), OCH$_3$ 6.10 ppm, (signal, 1H), NH 6.80 ppm, (dd, 1H), H$_5$ 7.00 ppm, (d, 1H), H$_7$ 7.20 ppm, (d, 1H), H$_4$

EXAMPLE 31

N-[2-(5-METHOXY-3-BENZOTHIAZOLINONYL)ETHYL]ACETAMIDE

STAGE A (5-METHOXY-3-BENZOTHIAZOLINONYL)ACETONITRILE

The procedure used is that described in Example 1, stage A, replacing 6-methoxybenzoxazolinone by 5-methoxybenzothiazolinone.

Recrystallization solvent: 95° strength alcohol Yield: 93% Melting point: 154°–156° C. Elemental analysis:

|  | C % | H % | N % |
|---|---|---|---|
| Calculated: | 54.52 | 3.66 | 12.72 |
| Found: | 54.88 | 3.47 | 12.76 |

Infrared spectrometry: (3080–2940) cm$^{-1}$, $\nu$ C—H 1680 cm$^{-1}$, $\nu$ CO(S—CO—N) (1630–1580) cm$^{-1}$, $\nu$ C=C (aromatic) Nuclear Magnetic Resonance Spectrometry (CDCl$_3$): 3.85 ppm, (s, 3H), OCH$_3$ 4.75 ppm, (s, 2H), CH$_2$—CN 6.75 ppm, (unresolved peaks, 2H), H$_4$, H$_6$ 7.30 ppm, (d, 1H), H$_7$

STAGE B 2-(5-METHOXY-3-BENZOTHIAZOLINONYL)ETHYLAMINE HYDROCHLORIDE

The procedure used is that described in Example 1, stage B, replacing (6-methoxy-3-benzoxazolinonyl)acetonitrile by (5-methoxy-3-benzothiazolinonyl)acetonitrile obtained in stage A.

Recrystallization solvent: 95° strength alcohol Yield: 86% Melting point: >260° C. Infrared spectrometry: (3100–2500) cm$^{-1}$, $\nu$ NH$_2$ salt 1640 cm$^{-1}$, $\nu$ CO(-S—CO—N) 1590 cm$^{-1}$, $\nu$ C=C (aromatic) Nuclear Magnetic Resonance Spectrometry (CDCl$_3$): 3.75 ppm, (s, 3H), OCH$_3$ 6.80 ppm, (dd, 1H), H$_6$ 7.25 ppm, (d, 1H), H$_4$ 7.50 ppm, (d, 1H), H$_7$ 8.50 ppm, (signal, 2H), NH$_2$ disappears in D$_2$O

STAGE C

N-[2-(5-METHOXY-3-BENZOTHIAZOLINONYL)ETHYL]ACETAMIDE

The procedure used is that described in Example 1, stage B, replacing 2-(6-methoxy-3-benzoxazolinonyl)ethylamine hydrochloride by 2-(5-methoxy-3-benzothiazolinonyl)ethylamine hydrochloride obtained in stage B.

Recrystallization solvent: Toluene Yield: 86% Melting point: 120°–122° C. Elemental analysis:

|  | C % | H % | N % |
|---|---|---|---|
| Calculated: | 54.11 | 5.29 | 10.52 |
| Found: | 54.42 | 5.28 | 10.49 |

Infrared spectrometry: 3280 cm$^{-1}$, $\nu$ N—H amide (3080–2840) cm$^{-1}$, $\nu$ C—H 1675 cm$^{-1}$, $\nu$ CO(-S—CO—N) 1650 cm$^{-1}$, $\nu$ CO (amide) 1610 cm$^{-1}$, $\nu$ C=C (aromatic) Nuclear Magnetic Resonance Spectrometry (CDCl$_3$): 1.93 ppm, (s, 3H), COCH$_3$ 3.55 ppm, (multiplet, 2H), CH$_2$—CH$_2$—NHCOCH$_3$ 3.80 ppm, (s, 3H), OCH$_3$ 4.15 ppm, (t, 2H), CH$_2$—CH$_2$—NHCOCH$_3$ 6.10 ppm, (signal, 1H), NH 6.75 ppm, (dd, 1H), H$_6$ 6.90 ppm, (d, 1H), H$_4$ 7.30 ppm, (d, 1H), H$_7$

EXAMPLE 32

N-[2-(5-Methoxy-3-Benzothiazolinonyl)Ethyl]Isobutyramide

The procedure used is that described in Example 31, replacing acetyl chloride in stage C by isobutyryl chloride.

Recrystallization solvent: Toluene/cyclohexane Yield: 87% Melting point: 158°–159° C. Elemental analysis:

|  | C % | H % | N % |
|---|---|---|---|
| Calculated: | 57.12 | 6.16 | 9.51 |
| Found: | 57.14 | 6.07 | 9.33 |

Infrared spectrometry: 3280 cm$^{-1}$, $\nu$ N—H (3080–2840) cm$^{-1}$, $\nu$ C—H 1675 cm$^{-1}$, $\nu$ CO(-S—CO—N) 1640 cm$^{-1}$, $\nu$ CO (amide) 1600 cm$^{-1}$, $\nu$ C=C (aromatic) Nuclear Magnetic Resonance Spectrometry (CDCl$_3$): 1.10 ppm, (s, 6H), CH(CH$_3$)$_2$ 2.25 ppm, (multiplet, 1H), CH 3.58 ppm, (multiplet, 2H), CH$_2$NHCO 3.85 ppm, (s, 3H), OCH$_3$ 4.10 ppm, (t, 2H), CH$_2$CH$_2$NHCO 6.15 ppm, (signal, 1H), NH 6.70 ppm, (dd, 1H), H$_6$ 6.80 ppm, (d, 1H), H$_4$ 7.26 ppm, (d, 1H), H$_7$

EXAMPLE 33

N-[2-(6-Methoxy-3-Benzothiazolinonyl)Ethyl]Isobutyramide

The procedure used is that described in Example 31, replacing acetyl chloride in stage C by isobutyryl chloride.

Recrystallization solvent: Toluene/cyclohexane Yield: 85% Melting point: 136°–138° C. Elemental analysis:

|  | C % | H % | N % |
|---|---|---|---|
| Calculated: | 57.12 | 6.16 | 9.51 |
| Found: | 57.44 | 6.35 | 9.72 |

Infrared spectrometry: 3300 cm$^{-1}$, $\nu$ N—H (3080–2840) cm$^{-1}$, $\nu$ C—H 1680 cm$^{-1}$, $\nu$ CO(-S—CO—N) 1640 cm$^{-1}$, $\nu$ CO (amide) 1600 cm$^{-1}$, $\nu$ C=C (aromatic) Nuclear Magnetic Resonance Spectrometry (CDCl$_3$): 1.10 ppm, (d, 6H), CH(CH$_3$)$_2$ 2.25 ppm, (multiplet, 1H), CH 3.80 ppm, (s, 3H), OCH$_3$ 6.10 ppm, (signal, 1H), NH 6.85 ppm, (dd, 1H), H$_5$ 7.00 ppm, (d, 1H), H$_7$ 7.20 ppm, (d, 1H), H$_4$

EXAMPLES 34 TO 58

Using the procedure described in Examples 5 to 29, but replacing 2-(6-methoxy-3-benzoxazolinonyl)ethylamine hydrochloride in stage C by 2-(6-methoxy-3-benzothiazolinonyl)ethylamine hydrochloride, the following are obtained, respectively:

EXAMPLE 34
N-[2-(6-Methoxy-3-Benzothiazolinonyl)Ethyl]-Phenylacetamide

EXAMPLE 35
N-[2-(6-Methoxy-3-Benzothiazolinonyl)Ethyl]-(2-Oxo-1-Pyrrolidinyl)Acetamide

EXAMPLE 36
N-[2-(6-Methoxy-3-Benzothiazolinonyl)Ethyl]-(2-Oxo-1-Pyrrolidinyl)-4-Chlorobutyramide

EXAMPLE 37
N-[2-(6-Methoxy-3-Benzothiazolinonyl)Ethyl]-2-Pyrrolidinone

EXAMPLE 38
N-[2-(6-Methoxy-3-Benzothiazolinonyl)Ethyl]-2-Bromoacetamide

EXAMPLE 39
N-[2-(6-Methoxy-3-Benzothiazolinonyl)Ethyl]-2-Morpholinoacetamide

EXAMPLE 40
N-[2-(6-Methoxy-3-Benzothiazolinonyl)Ethyl]-2-{4-(2,3,4-Trimethoxyphenyl)Methyl]-1-Piperazinyl-}Acetamide

EXAMPLE 41
N-[2-(6-Methoxy-3-Benzothiazolinonyl)Ethyl]-N-Methylacetamide

EXAMPLE 42
N-[2-(6-Methoxy-3-Benzothiazolinonyl)Ethyl]Benzamide

EXAMPLE 43
N-[2-(6-Methoxy-3-Benzothiazolinonyl)Ethyl]-Para-Toluenecarboxamide

EXAMPLE 44
N-[2-(6-Methoxy-3-Benzothiazolinonyl)Ethyl]-4-Fluorobenzamide

EXAMPLE 45
N-[2-(6-Methoxy-3-Benzothiazolinonyl)Ethyl]-3-(Trifluoromethyl)Benzamide

EXAMPLE 46
N-[2-(6-Methoxy-3-Benzothiazolinonyl)Ethyl]-3,5-Dichlorobenzamide

EXAMPLE 47
N-[2-(6-Methoxy-3-Benzothiazolinonyl)Ethyl]Isonicotinamide

EXAMPLE 48
N-[2-(6-Methoxy-3-Benzothiazolinonyl)Ethyl]-2-Indolecarboxamide

EXAMPLE 49
N-[2-(6-Methoxy-3-Benzothiazolinonyl)Ethyl]-2-(Benzylamino)Acetamide

EXAMPLE 50
N-[2-(6-Methoxy-3-Benzothiazolinonyl)Ethyl]-2-(N',N'-Diethylamino)Acetamide

EXAMPLE 51
N-[2-(6-Methoxy-3-Benzothiazolinonyl)Ethyl]-2-Aminoacetamide

EXAMPLE 52
N-[2-(6-Methoxy-3-Benzothiazolinonyl)Ethyl]-2-[4-(4-Fluorophenyl)-1-Piperazinyl]Acetamide

EXAMPLE 53
N-[2-(6-Methoxy-3-Benzothiazolinonyl)Ethyl]-2-{4-[-3-(Trifluoromethyl)Phenyl]-1-Piperazinyl}Acetamide

EXAMPLE 54
N-[2-(6-Methoxy-3-Benzothiazolinonyl)Ethyl]Cyclohexanecarboxamide

EXAMPLE 55
N-[2-(6-Methoxy-3-Benzothiazolinonyl)Ethyl]Formamide

EXAMPLE 56
N-[2-(6-Methoxy-3-Benzothiazolinonyl)Ethyl]Cyclopropanecarboxamide

EXAMPLE 57
N-[2-(6-Methoxy-3-Benzothiazolinonyl)Ethyl]Valeramide

EXAMPLE 58
N-[2-(6-Methoxy-3-Benzothiazolinonyl)Ethyl]Cyclobutanecarboxamide By replacing 2-(6-methoxy-3-benzothiazolinonyl)ethylamine in Examples 34 to 58 by 2-(5-methoxy-3-benzothiazolinonyl)ethylamine, the products of the preceding examples methoxylated, respectively, at position 5 are obtained instead of the compounds methoxylated at position 6.

EXAMPLE 59
N-[2-(6-Methoxy-4-Benzoxazinonyl)Ethyl]Acetamide

By replacing 6-methoxybenzoxazolinone in Example 1, stage A, by 6-methoxybenzoxazinone, the following are obtained, respectively:
STAGE A
2-(6-METHOXY-4-BENZOXAZINONYL)ACETONITRILE
STAGE B
2-(6-METHOXY-4-BENZOXAZINONYL)ETHYLAMINE HYDROCHLORIDE
STAGE C
N-[3-(6-METHOXY-3-BENZOXAZINONYL)ETHYL]ACETAMIDE

EXAMPLE 60
N-[2-(7-Methoxy-4-Benzoxazinonyl)Ethyl]Acetamide

Using the procedure described in Example 1, but replacing 6-methoxybenzoxazolinone by 7-methoxybenzoxazinone, the following are obtained, respectively:
2-(7-METHOXY-4-BENZOXAZINONYL)ACETONITRILE
2-(7-METHOXY-4-BENZOXAZINONYL)ETHYLAMINE HYDROCHLORIDE
N-[2-(7-METHOXY-4-BENZOXAZINONYL)Ethyl]ACETAMIDE

EXAMPLE 61

N-[2-(3-Methyl-6-Benzoxazolinonyl)Ethyl]Acetamide 0.02 mol of 2-(3-methyl-6-benzoxazolinonyl)ethylamine hydrochloride described in Patent Application EP 0,110,781, is dissolved in a water/chloroform mixture. 0.02 mol of potassium carbonate is added and the mixture is left stirring for one hour.

It is cooled in an ice bath and 0.022 mol of acetyl chloride is then added. The mixture is kept stirring for 30 minutes. The chloroform phase is washed with water, dried over calcium chloride and taken to dryness. The residue is recrystallized in toluene.

Yield: 76% Melting point: 150° C. Infrared spectrometry: 2260 cm$^{-1}$, $\nu$ N—H (3080-2880) cm$^{-1}$, $\nu$ C—H 1775 cm$^{-1}$, $\nu$ CO(O—CO—N) 1640 cm$^{-1}$, $\nu$ CO (amide) 1615 cm$^{-1}$, $\nu$ C=C (aromatic) Nuclear Magnetic Resonance Spectrometry (CDCl$_3$): 1.96 ppm, (s, 3H), COCH$_3$ 2.84 ppm, (t, 2H), CH$_2$NH 3.43 ppm, (s, 3H), NCH$_3$ 3.50 ppm, (multiplet, 2H), CH$_2$—CH$_2$NH 5.60 ppm, (signal, 1H), NH 6.80 ppm, (d, 1H), H$_4$ 7.00 ppm, (unresolved peaks, 2H), H$_5$, H$_7$

EXAMPLE 62

N-[2-(3-Methyl-6-Benzothiazolinonyl)Ethyl]Acetamide

By replacing 2-(3-methyl-6-benzoxazolinonyl)ethylamine hydrochloride in Example 61 by 2-(3-methyl-6-benzothiazolinonyl)ethylamine hydrochloride, described in French Patent Application 90/11,866, the product of the title is obtained. Yield: 79% Melting point: 134°-136° C. Infrared spectrometry: 3280 cm$^{-1}$, $\nu$ N—H (3080-2860) cm$^{-1}$, $\nu$ C—H 1670 cm$^{-1}$, $\nu$ CO(-S—CO—N) 1630 cm$^{-1}$, $\nu$ CO (amide) 1600 cm$^{-1}$, $\nu$ C=C (aromatic) Nuclear Magnetic Resonance Spectrometry (CDCl$_3$): 1.96 ppm, (s, 3H), COCH$_3$ 2.85 ppm, (t, 2H), CH$_2$NHCOCH$_3$ 3.50 ppm, (unresolved peaks, 5H), CH$_2$NHCOCH$_3$ and NCH$_3$ 5.50 ppm, (signal, 1H), NH 6.95 ppm, (d, 1H), H$_4$ 7.20 ppm, (unresolved peaks, 2H), H$_5$, H$_7$

EXAMPLE 63

N-[2-(3-Methyl-6-Benzoxazolinonyl)Ethyl]Isobutyramide

Using the procedure described in Example 61, but replacing acetyl chloride by isobutyryl chloride, the product of the title is obtained.

Infrared spectrometry: 1760 cm$^{-1}$, $\nu$ CO (OCON) 1640 cm$^{-1}$, $\nu$ CO (amide)

EXAMPLE 64

N-[2-(3-Methyl-6-Benzoxazolinonyl)Ethyl]-Phenylacetamide

Using the procedure described in Example 61, but replacing acetyl chloride by phenacetyl chloride, the product of the title is obtained.

EXAMPLE 65

N-[2-(3-Methyl-6-Benzoxazolinonyl)Ethyl]-(2-Oxo-1-Pyrrolidinyl)Acetamide

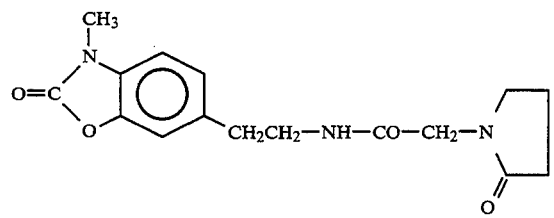

The procedure used is that described in Example 6, replacing 3-(2-aminoethyl)-6-methoxybenzoxazolinone by 2-(3-methyl-6-benzoxazolinonyl)ethylamine; the product of the title is obtained.

EXAMPLES 66 TO 88

Using the procedure described in Examples 7 to 29, but replacing 2-(6-methoxy-3-benzoxazolinonyl)ethylamine hydrochloride by 2-(3-methyl-6-benzoxazolinonyl)ethylamine hydrochloride, the following are obtained:

EXAMPLE 66

N-[2-(3-Methyl-6-Benzoxazolinonyl)Ethyl]-4-Chlorobutyramide

EXAMPLE 67

N-[2-(3-Methyl-6-Benzoxazolinonyl)Ethyl]-2-Pyrrolidinone

EXAMPLE 68

N-[2-(3-Methyl-6-Benzoxazolinonyl)Ethyl]-2-Bromoacetamide

EXAMPLE 69

N-[2-(3-Methyl-6-Benzoxazolinonyl)Ethyl]-2-Morpholinoacetamide

EXAMPLE 70

N-[2-(3-Methyl-6-Benzoxazolinonyl)Ethyl]-2-{4-[(2,3,4-Trimethoxyphenyl)Methyl]-1-Piperazinyl-}Acetamide

EXAMPLE 71

N-[2-(3-Methyl-6-Benzoxazolinonyl)Ethyl]-N-Methylacetamide

EXAMPLE 72
N-[2-(3-Methyl-6-Benzoxazolinonyl)Ethyl]Benzamide

EXAMPLE 73
N-[2-(3-Methyl-6-Benzoxazolinonyl)Ethyl]-Para-Toluenecarboxamide

EXAMPLE 74
N-[2-(3-Methyl-6-Benzoxazolinonyl)Ethyl]-4-Fluorobenzamide

EXAMPLE 75
N-[2-(3-Methyl-6-Benzoxazolinonyl)Ethyl]-3-(Trifluoromethyl)Benzamide

EXAMPLE 76
N-[2-(3-Methyl-6-Benzoxazolinonyl)Ethyl]-3,5-Dichlorobenzamide

EXAMPLE 77
N-[2-(3-Methyl-6-Benzoxazolinonyl)Ethyl]Isonicotinamide

EXAMPLE 78
N-[2-(3-Methyl-6-Benzoxazolinonyl)Ethyl]-2-Indolecarboxamide

EXAMPLE 79
N-[2-(3-Methyl-6-Benzoxazolinonyl)Ethyl]-2-(Benzylamino)Acetamide

EXAMPLE 80
N-[2-(3-Methyl-6-Benzoxazolinonyl)Ethyl]-2-(N',N'-Diethylamino)Acetamide

EXAMPLE 81
N-[2-(3-Methyl-6-Benzoxazolinonyl)Ethyl]-2-Aminoacetamide

EXAMPLE 82
N-[2-(3-Methyl-6-Benzoxazolinonyl)Ethyl]-2-[4-(4-Fluorophenyl)-1-Piperazinyl]Acetamide

EXAMPLE 83
N-[2-(3-Methyl-6-Benzoxazolinonyl)Ethyl]-2-{4-[3-(Trifluoromethyl)Phenyl)]-1-Piperazinyl}Acetamide

EXAMPLE 84
N-[2-(3-Methyl-6-Benzoxazolinonyl)Ethyl]Cyclohexanecarboxamide

EXAMPLE 85
N-[2-(3-Methyl-6-Benzoxazolinonyl)Ethyl]Formamide

EXAMPLE 86
N-[2-(3-Methyl-6-Benzoxazolinonyl)Ethyl]Cyclopropanecarboxamide

EXAMPLE 87
N-[2-(3-Methyl-6-Benzoxazolinonyl)Ethyl]Valeramide

EXAMPLE 88
N-[2-(3-Methyl-6-Benzoxazolinonyl)Ethyl]Cyclobutanecarboxamide

EXAMPLES 89 TO 113

Using the procedure described in Examples 5 to 20, but replacing 2-(6-methoxy-3-benzoxazolinonyl)ethylamine hydrochloride by 2-(3-methyl-6-benzothiazolinonyl)ethylamine hydrochloride, the following are obtained:

EXAMPLE 89
N-[2-(3-Methyl-6-Benzothiazolinonyl)Ethyl]-Phenylacetamide

EXAMPLE 90
N-[2-(3-Methyl-6-Benzothiazolinonyl)Ethyl]-(2-Oxo-1-Pyrrolidinyl)Acetamide

EXAMPLE 91
N-[2-(3-Methyl-6-Benzothiazolinonyl)Ethyl]-4-Chlorobutyramide

EXAMPLE 92
N-[2-(3-Methyl-6-Benzothiazolinonyl)Ethyl]-2-Pyrrolidinone

EXAMPLE 93
N-[2-(3-Methyl-6-Benzothiazolinonyl)Ethyl]-2-Bromoacetamide

EXAMPLE 94
N-[2-(3-Methyl-6-Benzothiazolinonyl)Ethyl]-2-Morpholinoacetamide

EXAMPLE 95
N-[2-(3-Methyl-6-Benzothiazolinonyl)Ethyl]-2-{4-[(2,3,4Trimethoxyphenyl)Methyl]-1-Piperazinyl}Acetamide

EXAMPLE 96
N-[2-(3-Methyl-6-Benzothiazolinonyl)Ethyl]-N-Methylacetamide

EXAMPLE 97
N-[2-(3-Methyl-6-Benzothiazolinonyl)Ethyl]Benzamide

EXAMPLE 98
N-[2-(3-Methyl-6-Benzothiazolinonyl)Ethyl]-Para-Toluenecarboxamide

EXAMPLE 99
N-[2-(3-Methyl-6-Benzothiazolinonyl)Ethyl]-4-Fluorobenzamide

EXAMPLE 100
N-[2-(3-Methyl-6-Benzothiazolinonyl)Ethyl]-3-(Trifluoromethyl)Benzamide

EXAMPLE 101
N-[2-(3-Methyl-6-Benzothiazolinonyl)Ethyl]-3,5-Dichlorobenzamide

EXAMPLE 102
N-[2-(3-Methyl-6-Benzothiazolinonyl)Ethyl]Isonicotinamide

EXAMPLE 103
N-[2-(3-Methyl-6-Benzothiazolinonyl)Ethyl]-2-Indolecarboxamide

EXAMPLE 104
N-[2-(3-Methyl-6-Benzothiazolinonyl)Ethyl]-2-(Benzylamino)Acetamide

EXAMPLE 105
N-[2-(3-Methyl-6-Benzothiazolinonyl)Ethyl]-2-(N',N'-

Diethylamino)Acetamide

EXAMPLE 106

N-[2-(3-Methyl-6-Benzothiazolinonyl)Ethyl]-2-Aminoacetamide

EXAMPLE 107

N-[2-(3-Methyl-6-Benzothiazolinonyl)Ethyl]-2-[4-(4-Fluorophenyl)-1-Piperazinyl]Acetamide

EXAMPLE 108

N-[2-(3-Methyl-6-Benzothiazolinonyl)Ethyl]-2-{4-[3-(Trifluoromethyl)Phenyl]-1-Piperazinyl}Acetamide

EXAMPLE 109

N-[2-(3-Methyl-6-Benzothiazolinonyl)Ethyl]Cyclohexanecarboxamide

EXAMPLE 110

N-[2-(3-Methyl-6-Benzothiazolinonyl)Ethyl]Formamide

EXAMPLE 111

N-[2-(3-Methyl-6-Benzothiazolinonyl)Ethyl]Cyclopropanecarboxamide

EXAMPLE 112

N-[2-(3-Methyl-6-Benzothiazolinonyl)Ethyl]Valeramide

EXAMPLE 113

N-[2-(3-Methyl-6-Benzothiazolinonyl)Ethyl]Cyclobutanecarboxamide

By replacing 2-(3-methyl-6-benzothiazolinonyl)ethylamine in Examples 89 to 113 by 2-(3-methyl-7-benzothiazolinonyl)ethylamine, obtained in Patent Application EP 174,811, products are obtained which are isomeric with those above, the side chain being at position 7 instead of at position 6:

EXAMPLE 114

N-[2-(3-Methyl-7-Benzothiazolinonyl)Ethyl]-Phenylacetamide

EXAMPLE 115

N-[2-(3-Methyl-7-Benzothiazolinonyl)Ethyl]-(2-Oxo-1-Pyrrolidinyl)Acetamide

EXAMPLE 116

N-[2-(3-Methyl-7-Benzothiazolinonyl)Ethyl]-4-Chlorobutyramide

EXAMPLE 117

N-[2-(3-Methyl-7-Benzothiazolinonyl)Ethyl]-2-Pyrrolidinone

EXAMPLE 118

N-[2-(3-Methyl-7-Benzothiazolinonyl)Ethyl]-2-Bromoacetamide

EXAMPLE 119

N-[2-(3-Methyl-7-Benzothiazolinonyl)Ethyl]-2-Morpholinoacetamide

EXAMPLE 120

N-[2-(3-Methyl-7-Benzothiazolinonyl)Ethyl]-2-{4-[(2,3,4-Trimethoxyphenyl)Methyl]-1-Piperazinyl}Acetamide

EXAMPLE 121

N-[2-(3-Methyl-7-Benzothiazolinonyl)Ethyl]-N-Methylacetamide

EXAMPLE 122

N-[2-(3-Methyl-7-Benzothiazolinonyl)Ethyl]Benzamide

EXAMPLE 123

N-[2-(3-Methyl-7-Benzothiazolinonyl)Ethyl]-Para-Toluenecarboxamide

EXAMPLE 124

N-[2-(3-Methyl-7-Benzothiazolinonyl)Ethyl]-4-Fluorobenzamide

EXAMPLE 125

N-[2-(3-Methyl-7-Benzothiazolinonyl)Ethyl]-3-(Trifluoromethyl)Benzamide

EXAMPLE 126

N-[2-(3-Methyl-7-Benzothiazolinonyl)Ethyl]-3,5-Dichlorobenzamide

EXAMPLE 127

N-[2-(3-Methyl-7-Benzothiazolinonyl)Ethyl]Isonicotinamide

EXAMPLE 128

N-[2-(3-Methyl-7-Benzothiazolinonyl)Ethyl]-2-Indolecarboxamide

EXAMPLE 129

N-[2-(3-Methyl-7-Benzothiazolinonyl)Ethyl]-2-(Benzylamino)acetamide

EXAMPLE 130

N-[2-(3-Methyl-7-Benzothiazolinonyl)Ethyl]-2-(N',N'-Diethylamino)Acetamide

EXAMPLE 131

N-[2-(3-Methyl-7-Benzothiazolinonyl)Ethyl]-2-Aminoacetamide

EXAMPLE 132

N-[2-(3-Methyl-7-Benzothiazolinonyl)Ethyl]-2-[4-(4Fluorophenyl)-1-Piperazinyl]Acetamide

EXAMPLE 133

N-[2-(3-Methyl-7-Benzothiazolinonyl)Ethyl]-2-{4-[3-(Trifluoromethyl)-1-Piperazinyl}Acetamide

EXAMPLE 134

N-[2-(3-Methyl-7-Benzothiazolinonyl)Ethyl]Cyclohexanecarboxamide

EXAMPLE 135

N-[2-(3-Methyl-7-Benzothiazolinonyl)Ethyl]Formamide

EXAMPLE 136

N-[2-(3-Methyl-7-Benzothiazolinonyl)Ethyl]Cyclopropanecarboxamide

EXAMPLE 137

N-[2-(3-Methyl-7-Benzothiazolinonyl)Ethyl]Valeramide

EXAMPLE 138

N-[2-(3-Methyl-7-Benzothiazolinonyl)Ethyl]Cyclobutanecarboxamide

EXAMPLES 139 TO 162

Using the procedure described in Examples 5 to 26, but replacing 2-(6-methoxy-3-benzoxazolinonyl)ethylamine hydrochloride in stage C by 2-(4-methyl-7-benzoxazinonyl)ethylamine hydrochloride, the following are obtained, respectively:

EXAMPLE 139
N-[2-(4-Methyl-7-Benzoxazinonyl)Ethyl]Phenylacetamide

EXAMPLE 140
N-[2-(4-Methyl-7-Benzoxazinonyl)Ethyl]-(2-Oxo-1-Pyrrolidinyl)Acetamide

EXAMPLE 141
N-[2-(4-Methyl-7-Benzoxazinonyl)Ethyl]-4-Chlorobutyramide

EXAMPLE 142
N-[2-(4-Methyl-7-Benzoxazinonyl)Ethyl]-2-Pyrrolidinone

EXAMPLE 143
N-[2-(4-Methyl-7-Benzoxazinonyl)Ethyl]-2-Bromoacetamide

EXAMPLE 144
N-[2-(4-Methyl-7-Benzoxazinonyl)Ethyl]-2-Morpholinoacetamide

EXAMPLE 145
N- [2-(4-Methyl-7-Benzoxazinonyl)Ethyl]-2-{4-[(2,3,4-Trimethoxyphenyl)Methyl]-1-Piperazinyl}Acetamide

EXAMPLE 146
N-[2-(4-Methyl-7-Benzoxazinonyl)Ethyl]-N-Methylacetamide

EXAMPLE 147
N-[2-(4-Methyl-7-Benzoxazinonyl)Ethyl]Benzamide

EXAMPLE 148
N-[2-(4-Methyl-7-Benzoxazinonyl)Ethyl]-Para-Toluenecarboxamide

EXAMPLE 149
N-[2-(4-Methyl-7-Benzoxazinonyl)Ethyl]-4-Fluorobenzamide

EXAMPLE 150
N-[2-(4-Methyl-7-Benzoxazinonyl)Ethyl]-3-(Trifluoromethyl)Benzamide

EXAMPLE 151
N-[2-(4-Methyl-7-Benzoxazinonyl)Ethyl]-3,5-Dichlorobenzamide

EXAMPLE 152
N-[2-(4-Methyl-7-Benzoxazinonyl)Ethyl]Isonicotinamide

EXAMPLE 153
N-[2-(4-Methyl-7-Benzoxazinonyl)Ethyl]-2-Indolecarboxamide

EXAMPLE 154
N-[2-(4-Methyl-7-Benzoxazinonyl)Ethyl]-2-(Benzylamino)Acetamide

EXAMPLE 155
N-[2-(4-Methyl-7-Benzoxazinonyl)Ethyl]-2-(N',N'-Diethylamino)Acetamide

EXAMPLE 156
N-[2-(4-Methyl-7-Benzoxazinonyl)Ethyl]-2-Aminoacetamide

EXAMPLE 157
N-[2-(4-Methyl-7-Benzoxazinonyl)Ethyl]-2-[4-(4-Fluorophenyl)-1-Piperazinyl)Acetamide

EXAMPLE 158
N-[2-(4-Methyl-7-Benzoxazinonyl)Ethyl]-2-{4-[3-(Trifluoromethyl)Phenyl]-1-Piperazinyl}Acetamide

EXAMPLE 159
N-[2-(4-Methyl-7-Benzoxazinonyl)Ethyl]Cyclohexanecarboxamide

EXAMPLE 160
N-[2-(4-Methyl-7-Benzoxazinonyl)Ethyl]Formamide

EXAMPLE 161
N-[2-(4-Methyl-7-Benzoxazinonyl)Ethyl]Cyclopropanecarboxamide

EXAMPLE 162
N-[2-(4-Methyl-7-Benzoxazinonyl)Ethyl]Valeramide

EXAMPLE 163
N-[2-(4-Methyl-7-Benzoxazinonyl)Ethyl]Cyclobutanecarboxamide

Using the procedure described in Examples 5 to 29, but replacing 2-(6-methoxy-3-benzoxazolinonyl)ethylamine hydrochloride in stage C by 2-(4-methyl 6-benzoxazinonyl)ethylamine hydrochloride, described in Patent Application FR 90/11,866 the following are obtained:

EXAMPLE 164
N-[2-(4-Methyl-6-Benzoxazinonyl)Ethyl]Phenylacetamide

EXAMPLE 165
N-[2-(4-Methyl-6-Benzoxazinonyl)Ethyl]-(2-Oxo-1-Pyrrolidinyl)Acetamide

EXAMPLE 166
N-[2-(4-Methyl-6-Benzoxazinonyl)Ethyl]-4-Chlorobutyramide

EXAMPLE 167
N-[2-(4-Methyl-6-Benzoxazinonyl)Ethyl]-2-Pyrrolidinone

EXAMPLE 168
N-[2-(4-Methyl-6-Benzoxazinonyl)Ethyl]-2-Bromoacetamide

EXAMPLE 169
N-[2-(4-Methyl-6-Benzoxazinonyl)Ethyl]-2-Morpholinoacetamide

EXAMPLE 170
N-[2-(4-Methyl-6-Benzoxazinonyl)Ethyl]-2-{4-[(2,3,4-Trimethoxyphenyl)Methyl-1-Piperazinyl}Acetamide

EXAMPLE 171
N-[2-(4-Methyl-6-Benzoxazinonyl)Ethyl]-N-Methylacetamide

EXAMPLE 172
N-[2-(4-Methyl-6-Benzoxazinonyl)Ethyl]Benzamide

EXAMPLE 173
N-[2-(4-Methyl-6-Benzoxazinonyl)Ethyl]-Para-Toluenecarboxamide

EXAMPLE 174
N-[2-(4-Methyl-6-Benzoxazinonyl)Ethyl]-4-Fluorobenzamide

EXAMPLE 175
N-[2-(4-Methyl-6-Benzoxazinonyl)Ethyl]-3-(Trifluoromethyl)Benzamide

EXAMPLE 176
N-[2-(4-Methyl-6-Benzoxazinonyl)Ethyl]-3,5-Dichlorobenzamide

EXAMPLE 177
N-[2-(4-Methyl-6-Benzoxazinonyl)Ethyl]Isonicotinamide

EXAMPLE 178
N-[2-(4-Methyl-6-Benzoxazinonyl)Ethyl]-2-Indolecarboxamide

EXAMPLE 179
N-[2-(4-Methyl-6-Benzoxazinonyl)Ethyl]-2-(Benzylamino)Acetamide

EXAMPLE 180
N-[2-(4-Methyl-6-Benzoxazinonyl)Ethyl]-2-(N',N'-Diethylamino)Acetamide

EXAMPLE 181
N-[2-(4-Methyl-6-Benzoxazinonyl)Ethyl]-2-Aminoacetamide

EXAMPLE 182
N-[2-(4-Methyl-6-Benzoxazinonyl)Ethyl]-2-[4-(4-Fluorophenyl)-1-Piperazinyl]Acetamide

EXAMPLE 183
N-[2-(4-Methyl-6-Benzoxazinonyl)Ethyl]-2-{4-[3-(Trifluoromethyl)Phenyl]-1-Piperazinyl}Acetamide

EXAMPLE 184
N-[2-(4-Methyl-6-Benzoxazinonyl)Ethyl]Cyclohexanecarboxamide

EXAMPLE 185
N-[2-(4-Methyl-6-Benzoxazinonyl)Ethyl]Formamide

EXAMPLE 186
N-[2-(4-Methyl-6-Benzoxazinonyl)Ethyl]cyclopropanecarboxamide

EXAMPLE 187
N-[2-(4-Methyl-6-Benzoxazinonyl)Ethyl]Valeramide

EXAMPLE 188
N-[2-(4-Methyl-6-Benzoxazinonyl)Ethyl]Cyclobutanecarboxamide

EXAMPLE 189
N-[2-(6-Methoxy-3-Benzoxazinonyl)Ethyl]-2-Methylcyclopropanecarboxamide
$R_2$=2-METHYLCYCLOPROPYL Using the procedure described in Example 1, but replacing acetyl chloride in stage C by 2-methylcyclopropanecarbonyl chloride, the product of the title is obtained.

EXAMPLE 190
N-[2-(5-Methoxy-3-Benzoxazolinonyl)Ethyl]-2-Methylcyclopropanecarboxamide Using the procedure described in Example 189, but replacing 6-methoxybenzoxazolinone in stage A by 5-methoxybenzoxazolinone, the product of the title is obtained.

EXAMPLE 191
N-[2-(5-Methoxy-3-Benzoxazolinonyl)Ethyl]Cyclopropanecarboxamide Using the procedure described in Example 1, but replacing 6-methoxybenzoxazolinone in stage A by 5-methoxybenzoxazolinone, and acetyl chloride by cyclopropanecarbonyl chloride, the product of the title is obtained.

Recrystallization: toluene Melting point: 150°-151° C.

EXAMPLE 192
N-[2-(5-Methoxy-3-Benzothiazolinonyl)Ethyl]Cyclopropanecarboxamide Using the procedure described in Example 1, but replacing 6-methoxybenzoxazolinone in stage A by 5-methoxybenzothiazolinone, and acetyl chloride by cyclopropanecarbonyl chloride, the product of the title is obtained.

Recrystallization: toluene Melting point: 135°-136° C.

Using the procedure described in Examples 1 and 4 to 29, but replacing 6-methoxybenzoxazolinone by benzoxazolinone itself, the following are obtained:
N-[2-(3-BENZOXAZOLINONYL)ETHYL]ACETAMIDE
N-[2-(3-BENZOXAZOLINONYL)ETHYL]ISOBUTYRAMIDE
N-[2-(3-BENZOXAZOLINONYL)ETHYL]-PHENYLACETAMIDE
N-[2-(3-BENZOXAZOLINONYL)ETHYL]-(2-OXO-1-PYRROLIDINYL)ACETAMIDE
N-[2-(3-BENZOXAZOLINONYL)ETHYL]-4-CHLOROBUTYRAMIDE
N-[2-(3-BENZOXAZOLINONYL)ETHYL]-2-PYRROLIDINONE
N-[2-(3-BENZOXAZOLINONYL)ETHYL]-2-BROMOACETAMIDE
N-[2-(3-BENZOXAZOLINONYL)ETHYL]-2-MORPHOLINOACETAMIDE
N-[2-(3-BENZOXAZOLINONYL)ETHYL]-2-{4-[(2,3,4-TRIMETHOXYPHENYL)METHYL]-1-PIPERAZINYL}ACETAMIDE
N-[2-(3-BENZOXAZOLINONYL)ETHYL]-N-

METHYLACETAMIDE
N-[2-(3-BENZOXAZOLINONYL)ETHYL]BENZAMIDE
N-[2-(3-BENZOXAZOLINONYL)ETHYL]-PARA-TOLUENECARBOXAMIDE
N-[2-(3-BENZOXAZOLINONYL)ETHYL]-4-FLUOROBENZAMIDE
N-[2-(3-BENZOXAZOLINONYL)ETHYL]-2-[4-(4-FLUOROPHENYL)-1-PIPERAZINYL]ACETAMIDE
N-[2-(3-BENZOXAZOLINONYL)ETHYL]-3-(TRIFLUOROMETHYL)BENZAMIDE
N-[2-(3-BENZOXAZOLINONYL)ETHYL]-3,5-DICHLOROBENZAMIDE
N-[2-(3-BENZOXAZOLINONYL)ETHYL]ISONICOTINAMIDE
N-[2-(3-BENZOXAZOLINONYL)ETHYL]-2-INDOLECARBOXAMIDE
N-[2-(3-BENZOXAZOLINONYL)ETHYL]-2-(BENZYLAMINO)ACETAMIDE
N-[2-(3-BENZOXAZOLINONYL)ETHYL]-2-(N',N'-DIETHYLAMINO)ACETAMIDE
N-[2-(3-BENZOXAZOLINONYL)ETHYL]-2-AMINOACETAMIDE
N-[2-(3-BENZOXAZOLINONYL)ETHYL]-2-{4-[3-(TRIFLUOROETHYL)PHENYL]-1PIPERAZINYL}ACETAMIDE
N-[2-(3-BENZOXAZOLINONYL)ETHYL]CYCLOHEXANECARBOXAMIDE
N-[2-(3-BENZOXAZOLINONYL)ETHYL]FORMAMIDE
N-[2-(3-BENZOXAZOLINONYL)ETHYL]CYCLOPROPANECARBOXAMIDE
N-[2-(3-BENZOXAZOLINONYL)ETHYL]VALERAMIDE
N-[2-(3-BENZOXAZOLINONYL)ETHYL]CYCLOBUTANECARBOXAMIDE

Using the procedure described in Examples 1 and 4 to 29, but replacing 6-methoxybenzoxazolinone by benzothiazolinone, the following are obtained:
N-[2-(3-BENZOTHIAZOLINONYL)ETHYL]ACETAMIDE
N-[2-(3-BENZOTHIAZOLINONYL)ETHYL]ISOBUTYRAMIDE
N-[2-(3-BENZOTHIAZOLINONYL)ETHYL]-PHENYLACETAMIDE
N-[2-(3-BENZOTHIAZOLINONYL)ETHYL]-(2-OXO-1-PYRROLIDINYL)ACETAMIDE
N-[2-(3-BENZOTHIAZOLINONYL)ETHYL]-4-CHLOROBUTYRAMIDE
N-[2-(3-BENZOTHIAZOLINONYL)ETHYL]-2-PYRROLIDINONE
N-[2-(3-BENZOTHIAZOLINONYL)ETHYL]-2-BROMOACETAMIDE
N-[2-(3-BENZOTHIAZOLINONYL)ETHYL]-2-MORPHOLINOACETAMIDE
N-[2-(3-BENZOTHIAZOLINONYL)ETHYL]-2-{4-[(2,3,4-TRIMETHOXYPHENYL)METHYL]-1-PIPERAZINYL}ACETAMIDE
N-[2-(3-BENZOTHIAZOLINONYL)ETHYL]-N-METHYLACETAMIDE
N-[2-(3-BENZOTHIAZOLINONYL)ETHYL]-BENZAMIDE
N-[2-(3-BENZOTHIAZOLINONYL)ETHYL]-PARA-TOLUENECARBOXAMIDE
N-[2-(3-BENZOTHIAZOLINONYL)ETHYL]-4-FLUOROBENZAMIDE
N-[2-(3-BENZOTHIAZOLINONYL)ETHYL]-2-[4-(4-FLUOROPHENYL)-1-PIPERAZINYL]ACETAMIDE
N-[2-(3-BENZOTHIAZOLINONYL)ETHYL]-3-(TRIFLUOROMETHYL)BENZAMIDE
N-[2-(3-BENZOTHIAZOLINONYL)ETHYL]-3,5-DICHLOROBENZAMIDE
N-[2-(3-BENZOTHIAZOLINONYL)ETHYL]ISONICOTINAMIDE
N-[2-(3-BENZOTHIAZOLINONYL)ETHYL]-2-INDOLECARBOXAMIDE
N-[2-(3-BENZOTHIAZOLINONYL)ETHYL]-2-(BENZYLAMINO)ACETAMIDE
N-[2-(3-BENZOTHIAZOLINONYL)ETHYL]-2-(N',N'-DIETHYLAMINO)ACETAMIDE
N-[2-(3-BENZOTHIAZOLINONYL)ETHYL]-2-AMINOACETAMIDE
N-[2-(3-BENZOTHIAZOLINONYL)ETHYL]-2-{4-[3-(TRIFLUOROMETHYL)PHENYL]-1-PIPERAZINYL}ACETAMIDE
N-[2-(3-BENZOTHIAZOLINONYL)ETHYL]CYCLOHEXANECARBOXAMIDE
N-[2-(3-BENZOTHIAZOLINONYL)ETHYL]-FORMAMIDE
N-[2-(3-BENZOTHIAZOLINONYL)ETHYL]CYCLOPROPANECARBOXAMIDE
N-[2-(3-BENZOTHIAZOLINONYL)ETHYL]-VALERAMIDE
N-[2-(3-BENZOTHIAZOLINONYL)ETHYL]CYCLOBUTANECARBOXAMIDE Using the procedure described in Examples 61 to 88, but replacing 3-methylbenzoxazolinone by benzoxazolinone itself, the following are obtained:
N-[2-(6-BENZOXAZOLINONYL)ETHYL]ACETAMIDE
N-[2-(6-BENZOXAZOLINONYL)ETHYL]ISOBUTYRAMIDE
N-[2-(6-BENZOXAZOLINONYL)ETHYL]PHENYLACETAMIDE
N-[2-(6-BENZOXAZOLINONYL)ETHYL]-(2-OXO-1-PYRROLIDINYL)ACETAMIDE
N-[2-(6-BENZOXAZOLINONYL)ETHYL]-4-CHLOROBUTYRAMIDE
N-[2-(6-BENZOXAZOLINONYL)ETHYL]-2-PYRROLIDINONE
N-[2-(6-BENZOXAZOLINONYL)ETHYL]-2-BROMOACETAMIDE
N-[2-(6-BENZOXAZOLINONYL)ETHYL]-2-MORPHOLINOACETAMIDE
N-[2-(3-BENZOXAZOLINONYL)ETHYL]-2-{4-[(2,3,4-TRIMETHOXYPHENYL)METHYL]-1-PIPERAZINYL}ACETAMIDE
N-[2-(6-BENZOXAZOLINONYL)ETHYL]-N-METHYLACETAMIDE
N-[2-(6-BENZOXAZOLINONYL)ETHYL]BENZAMIDE
N-[2-(6-BENZOXAZOLINONYL)ETHYL]-PARA-TOLUENECARBOXAMIDE
N-[2-(6-BENZOXAZOLINONYL)ETHYL]-4-FLUOROBENZAMIDE
N-[2-(6-BENZOXAZOLINONYL)ETHYL]-2-[4-(4-FLUOROPHENYL)-1-PIPERAZINYL]ACETAMIDE
N-[2-(6-BENZOXAZOLINONYL)ETHYL]-3-(TRIFLUOROMETHYL)BENZAMIDE
N-[2-(6-BENZOXAZOLINONYL)ETHYL]-3,5-DICHLOROBENZAMIDE N-[2-(6-BENZOXAZOLINONYL)ETHYL]ISONICOTINAMIDE
N-[2-(6-BENZOXAZOLINONYL)ETHYL]-2-INDOLECARBOXAMIDE
N-[2-(6-BENZOXAZOLINONYL)ETHYL]-2-(BENZYLAMINO)ACETAMIDE
N-[2-(6-BENZOXAZOLINONYL)ETHYL]-2-(N',N'-DIETHYLAMINO)ACETAMIDE
N-[2-(6-BENZOXAZOLINONYL)ETHYL]-2-AMINOACETAMIDE
N-[2-(6-BENZOXAZOLINONYL)ETHYL]-2-{4-[3-(TRIFLUOROMETHYL)PHENYL]-1-PIPERAZINYL}ACETAMIDE
N-[2-(6-BENZOXAZOLINONYL)ETHYL]CYCLOHEXANECARBOXAMIDE
N-[2-(6-BENZOXAZOLINONYL)ETHYL]FORMAMIDE
N-[2-(6-BENZOXAZOLINONYL)ETHYL]CYCLOPROPANECARBOXAMIDE
N-[2-(6-BENZOXAZOLINONYL)ETHYL]VALERAMIDE
N-[2-(6-BENZOXAZOLINONYL)ETHYL]CYCLOBUTANECARBOXAMIDE Using the procedure described in Examples 61 to 88, but replacing 3-methylbenzoxazolinone by benzothiazolinone itself, the following are obtained:

N-[2-(6-BENZOTHIAZOLINONYL)ETHYL]ACETAMIDE
N-[2-(6-BENZOTHIAZOLINONYL)ETHYL]ISOBUTYRAMIDE
N-[2-(6-BENZOTHIAZOLINONYL)ETHYL]PHENYLACETAMIDE
N-[2-(6-BENZOTHIAZOLINONYL)ETHYL]-(2-OXO-1-PYRROLIDINYL)ACETAMIDE
N-[2-(6-BENZOTHIAZOLINONYL)ETHYL]-4-CHLOROBUTYRAMIDE
N-[2-(6-BENZOTHIAZOLINONYL)ETHYL]-2-PYRROLIDINONE
N-[2-(6-BENZOTHIAZOLINONYL)ETHYL]-2-BROMOACETAMIDE
N-[2-(6-BENZOTHIAZOLINONYL)ETHYL]-2-MORPHOLINOACETAMIDE
N-[2-(3-BENZOTHIAZOLINONYL)ETHYL]-2-{4-[(2,3,4-TRIMETHOXYPHENYL)METHYL]-1-PIPERAZINYL}ACETAMIDE
N-[2-(6-BENZOTHIAZOLINONYL)ETHYL]-N-METHYLACETAMIDE
N-[2-(6-BENZOTHIAZOLINONYL)ETHYL]BENZAMIDE
N-[2-(6-BENZOTHIAZOLINONYL)ETHYL]PARA-TOLUENECARBOXAMIDE
N-[2-(6-BENZOTHIAZOLINONYL)ETHYL]-4-FLUOROBENZAMIDE
N-[2-(6-BENZOTHIAZOLINONYL)ETHYL]-2-[4-(4-FLUOROPHENYL)-1-PIPERAZINYL]ACETAMIDE
N-[2-(6-BENZOTHIAZOLINONYL)ETHYL]-3-(TRIFLUOROMETHYL)BENZAMIDE
N-[2-(6-BENZOTHIAZOLINONYL)ETHYL]-3,5-DICHLOROBENZAMIDE
N-[2-(6-BENZOTHIAZOLINONYL)ETHYL]ISONICOTINAMIDE
N-[2-(6-BENZOTHIAZOLINONYL)ETHYL]-2-INDOLECARBOXAMIDE
N-[2-(6-BENZOTHIAZOLINONYL)ETHYL]-2-(BENZYLAMINO)ACETAMIDE
N-[2-(6-BENZOTHIAZOLINONYL)ETHYL]-2-(N',N'-DIETHYLAMINO)ACETAMIDE
N-[2-(6-BENZOTHIAZOLINONYL)ETHYL]-2-AMINO)ACETAMIDE
N-[2-(6-BENZOTHIAZOLINONYL)ETHYL]-2-{4-[3-(TRIFLUOROMETHYL)PHENYL]-1-PIPERAZINYL}ACETAMIDE
N-[2-(6-BENZOTHIAZOLINONYL)ETHYL]CYCLOHEXANECARBOXAMIDE
N-[2-(6-BENZOTHIAZOLINONYL)ETHYL]FORMAMIDE
N-[2-(6-BENZOTHIAZOLINONYL)ETHYL]CYCLOPROPANECARBOXAMIDE
N-[2-(6-BENZOTHIAZOLINONYL)ETHYL]VALERAMIDE
N-[2-(6-BENZOTHIAZOLINONYL)ETHYL]CYCLOBUTANECARBOXAMIDE

PHARMACOLOGICAL STUDY OF THE COMPOUNDS OF THE INVENTION

EXAMPLE A

Study of Acute Toxicity

Acute toxicity was assessed after oral administration to batches of 8 mice (26±2 grams). The animals were observed at regular intervals during the first day and daily during the two weeks following treatment. The $LD_{50}$ causing the death of 50% of the animals was evaluated.

The $LD_{50}$ of the products tested is greater than 1000 $mg.kg^{-1}$ for most of the compounds studied, which indicates the low toxicity of the compounds of the invention.

EXAMPLE B

Activity Measurement

The animals are placed in plexiglass boxes equipped with photoelectric cells placed in a darkened environment. Six animals are tested simultaneously, and the number of interruptions of the photoelectric beams by each animal is recorded by computer during one hour.

The test compounds are administered intraperitoneally immediately before placing the animals in the apparatus.

The products of the invention decrease the animals' activity.

EXAMPLE C

Four Plates Test

The products of the invention are administered via the esophagus to batches of ten mice. One batch receives acacia syrup.

30 minutes after administration of the test products, the animals are placed in compartments the floor of which comprises four metal plates. Every time the animal passes from one plate to another, it receives a mild electric shock (0.35 mA). The number of transfers from one plate to another is recorded during one minute. After administration, the compounds of the invention significantly increase the number of transfers from one plate to another, demonstrating the anxiolytic activity of the compounds of the invention.

EXAMPLE D

Activity of the Products of the Invention Relation to Ischemic Microcirculation

The experimental study was carried out on the cremaster muscles of male rats (Sprague-Dawley) after ligation of the common iliac artery.

The muscles were placed in a transparent chamber perfused with a bicarbonate buffer solution equilibrated with a 5:95% $CO_2/N_2$ gaseous mixture. The velocity of the red cells and the diameter of the first or second order arterioles irrigating the cremaster were measured, and the arteriolar blood flow was calculated. Identical data were obtained for four types of venules.

The same type of measurement was made simultaneously:
on the normally perfused cremaster,
on the ligated cremaster, that is to say the ischemic cremaster, 2, 7, 14 and 21 days after ligation.
Two group of animals were studied:
an untreated control group,
a group treated orally with a product of the invention at the rate of 0.1 mg.kg$^{-1}$ per day.

No difference was noted in the velocity of the red cells or in the diameter of the vessels in the normally irrigated cremaster muscles in the treated animals in comparison to the controls.

In contrast, in the ischemic cremaster muscle, the mean diameter of the arterioles was improved in the treated animals in comparison to the controls. The velocity of the red cells was normalized by treatment for 21 days.

In fact, in the treated animals, the velocity of the red cells and the blood flow measured 7 days after ligation show no significant difference from the values obtained in the non-ischemic cremaster. These results are obtained without modification of arterial blood pressure.

These results indicate that long-term treatment with a compound of the invention improves the microcirculation and irrigation with blood of ischemic areas.

EXAMPLE E

Stimulation of the Immune Response

Batches of six mice were administered sheep red cells. These batches of mice were then treated subcutaneously with the compounds of the invention for six days, and a control group was treated with a placebo. The mice were then left undisturbed for four weeks and thereafter received a booster injection of sheep red cells without receiving further administrations of a product of the invention. The immune response was evaluated 3 days after the booster injection. It statistically increased in the group treated with the compounds of the invention.

EXAMPLE F

Inhibition of Ovulation

Adult female rats with regular four-day cycles were used.

Daily vaginal smears were prepared, and rats were selected after showing at least two consecutive four-day cycles.

Each cycle consists of two days of diestrus, one day of proestrus and one day of estrus.

In the afternoon of the day of proestrus, luteinizing hormone is released into the blood by the pituitary. This hormone induces ovulation, which results in the presence of ova in the oviduct on the day of estrus.

The compounds of the invention are on set orally at midday on the day of estrus. The treated and control rats are sacrificed on the day of estrus. The oviducts are examined. A significant percentage decrease in the number of ova is noted in the oviducts of treated rats.

EXAMPLE G

Demonstration of Analgesic Activity

The activity against pain was investigated in mice (23-25 g) according to a protocol derived from the technique described by SIEGMUND (SIEGMUND E. A., R. A. CADMUS & GOLU, J. Pharm. Exp. Ther. 119, 1874, 1954). Mice, randomized in batches of 12 animals, received the treatment orally (excipient in the case of Controls) 1 hour before intraperitoneal injection of a 0.02% aqueous-alcoholic solution of phenyl-p-benzoquinone (Sigma). The writhing movements are counted between the 5th and 10th minute after injection.

It was apparent that some compounds of the invention possess analgesic activity.

EXAMPLE H

Potentiation of Barbiturate-Induced Sleep

Mice (22-25 g) are injected intraperitoneally with pentobarbital at 50 mg.kg$^{-1}$. The time of onset and the duration of sleep are measured. The animals are taken to be asleep when they lose the righting reflex. The test compounds are administered intraperitoneally 30 minutes before the barbiturate injection. The products of the invention increase the duration of pentobarbital-induced sleep.

EXAMPLE I

Text of Binding to Melatonin Receptors

Binding of the compounds of the invention to melatonin receptors was carried out according to conventional techniques. It is apparent that the compounds of the invention bind beneficially to melatonin receptors.

EXAMPLE J

Study of Hypoglycemic Activity

Male KK mice were placed in cages at the age of eight weeks. They are used for the experiment when their weight is greater than 40 grams at the age of 4-5 months.

The compound of the invention is suspended in acacia syrup. Each compound tested is administered orally 18 hours before blood sampling.

Blood is collected by sampling from the caudal. vein in a hematocrit tube, and then centrifuged. The plasma is collected and the blood sugar level assayed.

It is apparent that some compounds of the invention significantly decrease the blood sugar level.

EXAMPLE K

Study of the Influence of the Products of the Invention on Melatonin Synthesis

The products of the invention are administered intraperitoneally to rats (Sprague-Dawley) at doses 1, 5 and 25 mg.kg$^{-1}$. Three hours after administration, the animals are sacrificed and melatonin assayed radioimmunologically. The measurement is validated by performing parallel controls. A considerable increase is observed in the plasma melatonin level after administration of the products of the invention.

EXAMPLE L

PHARMACEUTICAL COMPOSITION: TABLETS

Tablets containing 30 mg of

N-[2-(3-methyl-6-benzoxazolinonyl)ethyl]acetamide

| | |
|---|---|
| N-[2-(3-methyl-6-benzoxazolinonyl)ethyl]acetamide | 30 g |
| Wheat starch | 15 g |
| Corn starch | 15 g |
| Lactose | 15 g |
| Magnesium stearate | 2 g |
| Silica | 1 g |
| Hydroxypropylcellulose | 2 g |

We claim:

1. A compound selected from those of formula (Ia)

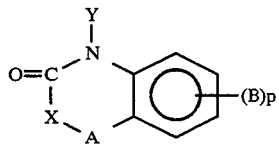

in which Y is —$CH_2$—$CH_2R'a$, wherein $R'a$ is NH—$R_1$ with $R_1$ being hydrogen or alkyl having 1 to 6 carbon atoms, inclusive, X is or a single bond, A is sulfur, B is alkoxy having 1 to 6 carbon atoms, inclusive, and p is 1, and soluble acid addition salts thereof when $R'a$ is —NH—$R_1$.

2. A compound of claim 1 which is selected from 2-(5-methoxy benzothiazolinon-3-yl)ethylamine and soluble acid addition salts thereof.

3. A compound of claim 1 which is selected from 2-(6-methoxy-benzothiazolinon-3-yl)ethylamine and soluble acid addition salts thereof.

* * * * *

UNITED STATES PATENT AND TRADEMARK OFFICE
CERTIFICATE OF CORRECTION

PATENT NO. : 5,386,034
DATED : January 31, 1995
INVENTOR(S) : Said Yous, Isabelle Lesieur, Patrick Depreux, Daniel H. Caignard, Bèatrice Guardiola, Gèrard Adam, Pierre Renard It is certified that error appears in the above-indentified patent and that said Letters Patent is hereby corrected as shown below:

```
Column  2, line 30; delete the "*" at the end of the line.
Column  2, line 59; delete the"-CH-" at the end of the line.
Column  2, line 60; insert "-CH" at the beginning of the line.
Column  3, line 48; "(V/B)" should read -- (IV/B) --
Column  4, line 55; insert the word "to" at the beginning of the
     line.
Column  5, line 49; insert "₁" at the end of the line, but
     before the hyphen to read -- R₁- --.
Column  5, line 50; delete the "₁" at the beginning of the line.
Column  7, line 30; at the end of the formula: "O" should read
```

J

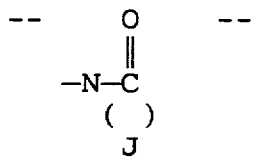

```
Column  9, line 36; "H₄ H7.05" should read -- H₄ H₆ 7.05 --
Column 10, line 17; delete the "(O- " at the end of the line.
     before the hyphen.
Column 10, line 18; insert the "(O-" at the beginning of the
     line to read with the rest of the formula.
Column 11, line 34; delete the "(O-" at the end of the line.
     before the hyphen.
Column 11, line 35; insert the "(O-" at the beginning of the
line        to read with the rest of the formula.
```

UNITED STATES PATENT AND TRADEMARK OFFICE
CERTIFICATE OF CORRECTION

PATENT NO. : 5,386,034

DATED : January 31, 1995

INVENTOR(S) : Said Yous, Isabelle Lesieur, Patrick Depreux, Daniel H. Caignard, Bèatrice Guardiola, Gèrard Adam, Pierre Renard It is certified that error appears in the above-indentified patent and that said Letters Patent is hereby corrected as shown below:

Column 11, line 59; delete the "(O—" at the end of the line, before the hyphen.
Column 11, line 60; insert the "(O—" at the beginning of the line to read with the rest of the formula.
Column 12, line 17; "(2-OXO1-" should read -- (2-OXO-1- --
Column 12, line 35; "33000" should read -- 3300 --
Column 12, line 42; "(6-Methoxy3-" should read -- (6-Methoxy-3- --
Column 12, line 48; delete the "(O—" at the end of the line, before the hyphen.
Column 12, line 49; insert the (O—" at the beginning of the line to read with the rest of the formula.
Column 12, line 66; delete the "(O—" at the end of the line, before the hyphen.
Column 12, line 67; insert the "(O—" at the beginning of the line to read with the rest of the formula.
Column 13, line 22; delete the "(O—" at the end of the line, before the hyphen.
Column 13, line 23; insert the "(O—" at the beginning of the line to read with the rest of the formula.
Column 14, line 12; "(6-Methoxy3-" should read -- (6-Methoxy-3- --
Column 16, line 14; "]-1PIPERAZINYL}" should read -- ]-1-PIPERAZINYL}--
Column 21, line 45; "$\underline{CH_2}NHCOCH_3$" should read -- $\underline{CH_2}CH_2NHCOCH_3$ --
Column 24, line 29; "[(2,3,4" should read -- [(2,3,4- --

UNITED STATES PATENT AND TRADEMARK OFFICE
CERTIFICATE OF CORRECTION

PATENT NO. : 5,386,034
DATED : January 31, 1995
INVENTOR(S) : Said Yous, Isabelle Lesieur, Patrick Depreux, Daniel H. Caignard, Bèatrice Guardiola, Gèrard Adam, Pierre Renard It is certified that error appears in the above-indentified patent and that said Letters Patent is hereby corrected as shown below:

Column 26, line 46; "[4-(4" should read -- [4-(4- --
Column 26, line 51; insert the word -- Phenyl] -- between the ")" and the "-1-"
Column 29, line 4; "Methyl-1" should read -- Methyl]-1 --
Column 30, line 33; start a new line with the word "Melting"
Column 30, line 44; start a new line with the word "Melting"
Column 31, line 27; "TRIFLUOROETHYL" should read
    -- TRIFLUOROMETHYL --
Column 31, line 28; insert a hyphen "-" after the "1" and before the "PIP"

Column 36, line 46; delete the "." between the words "caudal" and "vein"
Column 38, line 10; delete the "-N-" at the end of the line.
Column 38, line 11; insert the "-N" at the beginning of the line to read with the rest of the formula.

Signed and Sealed this

Twenty-fifth Day of July, 1995

BRUCE LEHMAN

*Attest:*

*Attesting Officer*  *Commissioner of Patents and Trademarks*